United States Patent
Woosley

(10) Patent No.: US 7,179,597 B2
(45) Date of Patent: Feb. 20, 2007

(54) GENETIC DIAGNOSIS FOR QT PROLONGATION RELATED ADVERSE DRUG REACTIONS

(75) Inventor: Raymond L. Woosley, Tucson, AZ (US)

(73) Assignee: Georgetown University, Washington, DC (US)

( * ) Notice: Subject to any disclaimer, the term of this patent is extended or adjusted under 35 U.S.C. 154(b) by 503 days.

(21) Appl. No.: 10/257,573

(22) PCT Filed: Apr. 13, 2001

(86) PCT No.: PCT/US01/12087

§ 371 (c)(1),
(2), (4) Date: Mar. 26, 2003

(87) PCT Pub. No.: WO01/79554

PCT Pub. Date: Oct. 25, 2001

(65) Prior Publication Data
US 2003/0211500 A1    Nov. 13, 2003

Related U.S. Application Data

(60) Provisional application No. 60/196,916, filed on Apr. 13, 2000.

(51) Int. Cl.
C12Q 1/68     (2006.01)
C12N 15/11    (2006.01)
C12N 15/12    (2006.01)

(52) U.S. Cl. .................. 435/6; 536/23.2; 536/23.5; 536/23.1; 536/24.31

(58) Field of Classification Search .............. None
See application file for complete search history.

(56) References Cited

FOREIGN PATENT DOCUMENTS

| WO | WO 99/13106 | 3/1999 |
|----|-------------|--------|
| WO | WO 00/06199 | 2/2000 |
| WO | WO 00/06772 | 2/2000 |

OTHER PUBLICATIONS

Ingelman-Sundberg, "Polymorphic human cytochrome P450 enzymes: an opportunity for individualized drug treatment", Trends in Pharmaceutical Sciences, 199, vol. 20, p. 342-349.

Abbott et al., "MiRP1 forms IKr potassium channels with HERG and Is associated with cardiac arrythmia", Cell, vol. 97, 1999, p. 175-187.

Drolet et al., "Block of the rapid component of the delayed rectifier potassium current by the prokinetic agent cisapride underlies drug-related lengthening of the QT interval", Circulation, 1998, vol. 97, p. 204-210.

Weyerbrock et al., "Rate-independent effects of the new class III antiarrhythmic agent ambasilide on transmembrane action potentials in human ventricular endomyocardium", Journal of Cardiovascular Pharmacology, 1997, vol. 30, p. 571-575.

Viskin, "Long QT syndromes and torsade de pointes", The Lancet, 1999, vol. 354, p. 1625-1633.

Larsen et al., "Recessive Romano-Ward syndrome associated with compound heterozygosity for two mutations in the KVLQT1 gene", European Journal of Human Genetics, 1999, vol. 7, p.724-728.

Itoh et al., Genomic organization and mutational analysis of KVLQT1, a gene responsible for familial long QT syndrome, Human Genetics, Sep. 1998, vol. 103, No. 3, p. 290-295.

Donger et al., KVLQT1 C-terminal missence mutation causes a forme fruste long QT-syndrome, Circulation, Nov. 4, 1997, vol. 96, No. 9, p. 2778-2781.

Schulze-Bahr, E., et al., "Molecular genetics of arrhythmias—a new paradigm," 2000, Z. Kardiol., 89 Suppl 4:IV1. pp. 12-15.

Hahnenberger K., et al., "Use of oligonucleotide array hybridization for genotyping CYP2D6 and CYP2C19," 1997, Clinical Pharmacology and Therapeutics, 61(2):165.

Wang, Q., et al., "Cardiac sodium channel mutations in patients with long QT syndrome, an inherited cardiac arrhythmia," 1995, Hum. Mol. Genet., 4(9):1603-7.

Gintant GA., "Azimilide causes reverse rate-dependent block while reducing both components of delayed-rectifier current in canine ventricular myocytes," 1998, J. Cardiovasc. Pharmacol., 31(6):945-53.

Selnick H.G., et al., "Class III antiarrhythmic activity in vivo by selective blockade of the slowly activating cardiac delayed rectifier potassium current IKs by (R)-2-(2,4-trifluoromethyl)-N-[2-oxo-5-phenyl-1-(2,2,2-trifluoroethyl)- 2, 3-dihydro-1H-benzo[e][1,4]diazepin-3-yl]acetamide," 1997, J. Med. Chem., 40(24):3865-8.

Schulze-Bahr, E., et al., "The LQT syndromes—current status of molecular mechanisms," 1999, Z. Kardiol., 88(4):245-54.

(Continued)

Primary Examiner—James Martinell
(74) Attorney, Agent, or Firm—Knobbe, Martens, Olson & Bear, LLP

(57) ABSTRACT

The specification is directed to a method of diagnosing whether a subject is predisposed to an adverse reaction to one or more pharmaceutical agents which may induce a prolonged QT interval or acquired LQTS in that individual. The diagnosis is genetic analysis of at least two polymorphisms or mutations which the individual may have, which are associated with an increased risk for prolonged QT intervals or Torsades de Pointes (TdP). Genetic screening for determining the predisposition of prolonged QT intervals induced by a pharmaceutical agent is performed by identifying genetic polymorphisms or mutations located in at least two classes of genes, wherein the genes are (1) LQT genes, (2) altered sensitivity genes (e.g., MiRP1) or (3) increased exposure genes (e.g., MDR genes or P450 cytochrome genes). The specification is also directed to compositions and kits for determining such predispositions to adverse drug reactions.

16 Claims, 5 Drawing Sheets

OTHER PUBLICATIONS

Wei Jian et al., "KCNE1 polymorphism confers risk of drug-induced long QT syndrome by altering kinetic properties of IKs potassium channels," Nov. 2, 1999, Circulation, 100(18 Suppl.):I.495; & 72nd Scientific Sessions of the American Heart Association; Atlanta, Georgia, USA; Nov. 7-10, 1999.

Wei Jian et al., "KCNE2 (Mirp1) mutations in acquired long QT syndrome," Nov. 2, 1999, Circulation, 100(18 Suppl.): I.495; & 72nd Scientific Sessions of the American Heart Association; Atlanta, Georgia, USA; Nov. 7-10, 1999.

Donger, C., et al., "KVLQT1 C-terminal missense mutation causes a forme fruste long-QT syndrome," 1997, Circulation, 96(9):2778-81.

Cavero, I., et al., "Drugs that prolong QT interval as an unwanted effect: assessing their likelihood of inducing hazardous cardiac dysrhythmias," 2000, Expert Opin. Pharmacother., 1(5):947-73.

Sesti, F., et al., "A common polymorphism associated with antibiotic-induced cardiac arrhythmia," 2000, Proc. Natl. Acad. Sci. U. S. A., 97(19):10613-8.

Busch., A.E., "Inhibition of I-Ks in guinea pig cardiac myocytes and guinea pig I-sK channels by the chromanol 293b", 1996, Pflugers Archiv. European Journal of Physiology,.432(6):1094-1096.

Mohler, Peter J., et al., "Ankyrin-B mutation causes type 4 long-QT cardiac arrhythmia and sudden cardiac death," Feb. 6, 2003, Nature, (London), 421(6923):634-639.

European Search Report dated Aug. 9, 2004 in PCT/US0112087.

Benson et al., "Missense Mutation in the Pore Region of *HERG* Causes Familial Long QT Syndrome," Circulation 93: 1791-5 (1996).

Chen et al., "Internal Duplication and Homology with Bacterial Transport Proteins in the *mdrl* (P-Glycoprotein) Gene from Multidrug-Resistant Human Cells," Cell 47: 381 (1986).

Donger et al., "KVLQT1 C-Terminal Missense Mutation Causes a Forme Fruste Long-QT Syndrome," Circulation 96: 2778-81 (1997).

Keating and Sanguinetti, "Molecular and Cellular Mechanisms of Cardiac Arrhythmias," Cell 104: 569 (2001).

Neyroud et al., "Heterozygous mutation in the pore of potassium channel gene *KvLQT1* causes an apparently normal phenotype in long QT syndrome," Eur J Hum Genet 6: 129-33 (1998).

Russell et al., "KVLQT1 mutations in three families with familial or sporadic long QT syndrome," Hum. Molec Genet 5: 1319-24 (1996).

Schulze-Bahr et al., "*KCNE1* mutations cause Jervell and Lange-Nielsen syndrome," Nature Genet 17: 267-8 (1997).

Wang, "Cardiac sodium channel mutations in patients with long QT syndrome, an inherited cardiac arrhythmia," Hum Molec Genet 4: 1603-7 (1995).

Wang et al., "Positional cloning of a novel potassium channel gene: *KVLQT1* mutations cause cardiac arrhythmias," Nature Genet 12: 17-23 (1996).

Wang et al., "Genetics, molecular mechanisms and management of long QT syndrome," Ann Med 30: 58 (1998).

SEQUENCE LISTING

<160> NUMBER OF SEQ ID NOS: 20

<210> SEQ ID NO 1
<211> LENGTH: 30
<212> TYPE: DNA
<213> ORGANISM: Artificial Sequence
<220> FEATURE:
<223> OTHER INFORMATION: Synthetic primer

<400> SEQUENCE: 1
cagaggagcc catttggtag tgaggcaggt         30

<210> SEQ ID NO 2
<211> LENGTH: 24
<212> TYPE: DNA
<213> ORGANISM: Artificial Sequence
<220> FEATURE:
<223> OTHER INFORMATION: Synthetic primer

<400> SEQUENCE: 2
ggtcccacgg aaatctgtct ctgt         24

<210> SEQ ID NO 3
<211> LENGTH: 21
<212> TYPE: DNA
<213> ORGANISM: Artificial Sequence
<220> FEATURE:
<223> OTHER INFORMATION: Synthetic primer

<400> SEQUENCE: 3
cacgcgcacg tgcccgtccc a         21

<210> SEQ ID NO 4
<211> LENGTH: 24
<212> TYPE: DNA
<213> ORGANISM: Artificial Sequence
<220> FEATURE:
<223> OTHER INFORMATION: Synthetic primer

<400> SEQUENCE: 4
ctctcgctcc gcacctcgcg caga                                    24

<210> SEQ ID NO 5
<211> LENGTH: 26
<212> TYPE: DNA
<213> ORGANISM: Artificial Sequence
<220> FEATURE:
<223> OTHER INFORMATION: Synthetic primer

<400> SEQUENCE: 5
ggactctgta cctcctatcc acgtca                                  26

<210> SEQ ID NO 6
<211> LENGTH: 26
<212> TYPE: DNA
<213> ORGANISM: Artificial Sequence
<220> FEATURE:
<223> OTHER INFORMATION: Synthetic primer

<400> SEQUENCE: 6
cctcggcccc tgcactgttt cccaga                                  26

<210> SEQ ID NO 7
<211> LENGTH: 27
<212> TYPE: DNA
<213> ORGANISM: Artificial Sequence
<220> FEATURE:
<223> OTHER INFORMATION: Synthetic primer

<400> SEQUENCE: 7
ggcgaccaga gatgggtgac caggctc                                 27

<210> SEQ ID NO 8
<211> LENGTH: 28
<212> TYPE: DNA
<213> ORGANISM: Artificial Sequence
<220> FEATURE:
<223> OTHER INFORMATION: Synthetic primer

<400> SEQUENCE: 8
gcgccaggcc taccttaggg atgcggga                                28

<210> SEQ ID NO 9
<211> LENGTH: 25
<212> TYPE: DNA
<213> ORGANISM: Artificial Sequence
<220> FEATURE:
<223> OTHER INFORMATION: Synthetic primer

<400> SEQUENCE: 9
gggagacaaa ccaggacctg ccaga                                   25

<210> SEQ ID NO 10
<211> LENGTH: 30
<212> TYPE: DNA
<213> ORGANISM: Artificial Sequence
<220> FEATURE:
<223> OTHER INFORMATION: Synthetic primer

<400> SEQUENCE: 10
catctgctca gcctcaacgt acccctgtct           30

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
tgccgccttc gccaaccact                       20

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
gtgcggagcg agagaccgag g                     21

<210> SEQ ID NO 13
<211> LENGTH: 18
<212> TYPE: DNA
<213> ORGANISM: Artificial Sequence
<220> FEATURE:
<223> OTHER INFORMATION: Synthetic primer

<400> SEQUENCE: 13
accaggcccc tccaccgg                         18

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
tctggtaggg gagcctcagc                       20

<210> SEQ ID NO 15
<211> LENGTH: 14
<212> TYPE: DNA
<213> ORGANISM: Artificial Sequence
<220> FEATURE:
<223> OTHER INFORMATION: Synthetic primer

<400> SEQUENCE: 15
ccaccaggcc ccct                             14

<210> SEQ ID NO 16
<211> LENGTH: 14
<212> TYPE: DNA
<213> ORGANISM: Artificial Sequence
<220> FEATURE:
<223> OTHER INFORMATION: Synthetic primer

<400> SEQUENCE: 16
gcaccaggcc ccgt                             14

<210> SEQ ID NO 17

-continued

```
<211> LENGTH: 18
<212> TYPE: DNA
<213> ORGANISM: Artificial Sequence
<220> FEATURE:
<223> OTHER INFORMATION: Synthetic primer

<400> SEQUENCE: 17
ttctcaaaag tctatggt                                                 18

<210> SEQ ID NO 18
<211> LENGTH: 18
<212> TYPE: DNA
<213> ORGANISM: Artificial Sequence
<220> FEATURE:
<223> OTHER INFORMATION: Synthetic primer

<400> SEQUENCE: 18
gccttgtgga ggagttga                                                 18

<210> SEQ ID NO 19
<211> LENGTH: 19
<212> TYPE: DNA
<213> ORGANISM: Artificial Sequence
<220> FEATURE:
<223> OTHER INFORMATION: Synthetic primer

<400> SEQUENCE: 19
gtccaggaag agattgatc                                                19

<210> SEQ ID NO 20
<211> LENGTH: 21
<212> TYPE: DNA
<213> ORGANISM: Artificial Sequence
<220> FEATURE:
<223> OTHER INFORMATION: Synthetic primer

<400> SEQUENCE: 20
cagaaactac ctcatcccca a                                             21
```

GENETIC DIAGNOSIS FOR QT PROLONGATION RELATED ADVERSE DRUG REACTIONS

CROSS REFERENCE TO RELATED APPLICATION

This application represents the U.S. National Stage of International Application No. PCT/US01/12087 filed Apr. 13, 2001, which claims the benefit of priority of U.S. Provisional Application No. 60/196,916, filed Apr. 13, 2000, the entirety of which is incorporated herein by reference.

FIELD OF THE INVENTION

The invention relates to methods of determining a predisposition for QT interval prolongation in a subject after the administration of a pharmaceutical agent or agents. Compositions and kits for determining said predispositions to the QT interval prolongation are also described.

BACKGROUND OF THE INVENTION

The invention relates to a method of screening a subject for a predisposition to an adverse drug reaction involving prolonged QT intervals. The genetic screening of patients for said predisposition focuses on genes associated with QT interval prolongation, including LQT genes, P-glycoprotein membrane pump proteins (P-gp), multidrug resistance genes and cytochrome P450-mediated drug metabolism genes.

I. LQT and Cytochrome P450 Genes and Polymorphisms

1. LQT Genes

Genes associated with long QT (LQT) syndrome (LQTS) include KVLQT1 (LQT1), HERG (LQT2), SCN5A (LQT3) and MinK (LQT5). A fifth gene locus exists on human chromosome 4 (e.g., LQT4). Recently, a sixth gene (LQT6) has been identified (Wang et al., Ann. Med. 30: 58–65 (1998)). All but LQT3 encode cardiac potassium ion ($K^+$) channel proteins; LQT3 encodes a cardiac sodium ion ($Na^+$) channel protein (Vincent, Annu. Rev. Med. 49: 263–74 (1998)). At least 180 mutations have been identified among these genes (Abbott et al., Cell 97: 175–87 (1999); Vincent. Annu. Rev. Med. 49: 263–74 (1998); Curran et al., Cell 80: 795–803 (1995); Berthet et al., Circulation 99: 1464–70 (1999); Dausse et al., J. Mol. Cell Cardiol. 28: 1609–15 (1996); Chen et al., J Biol. Chem. 274: 10113–8 (1999); and Sanguinetti et al., Proc. Natl. Acad. Sci. U.S.A. 93: 2208–12 (1996)). Some of these mutations cause altered ion channel function resulting in non-drug induced prolonged QT intervals and a propensity for Torsades de Pointes (TdP) (See, e.g., Berthet et al., Circulation 99: 1464–70 (1999)). Accordingly, genetic screening can be performed on subjects suspected of having long QT syndrome, as well as other patients (see, e.g., Satler et al., Hum. Genet. 102: 265–72 (1998)). Larson et al., Hum. Mutat. 13: 318–27 (1999) reported a high-throughout single strand polymorphism (SSCP) analysis for detecting point mutations associated with LQTS.

U.S. Pat. No. 5,599,673 claims two (e.g., HERG and SCN5A) of the six LQT genes. Two HERG-related genes have also been claimed (U.S. Pat. No. 5,986,081). International PCT Application WO 97/23598 describes a method of assessing a patient's risk for long QT syndrome (LQTS) by screening for genetic mutations in the MinK gene. However, these patents do not disclose methods of diagnosing a patient's predisposition to an adverse drug reaction involving elongation of the QT interval due to mutations in any of the LQT genes.

Drugs have been identified that cause QT interval prolongation, and thereby adverse drug reactions. Certain antihistamines, such as terfenadine (e.g., Seldane®) and astemizole (e.g., Hismanal®), reportedly block potassium channels (Woosley, Annu. Rev. Pharmacol. Toxicol. 36: 233–52 (1996)) and inhibit the HERG protein, and thereby were postulated to induce Torsades de Pointes (Wang et al., 1998). All antiarrhythmic drugs that lengthen repolarization reportedly can cause Torsades de Pointes (Drici et al., Circulation 94: 1471–4 (1996)). Additional non-cardiac and cardiac drugs capable of inducing QT prolongation including many that were identified by the inventor were released on Mar. 27, 1998 at the following web site: www.qtdrugs.org. However, Wei et al., Circulation 92:1–125 (1995) could not identify HERG or SCN5A gene mutations that were linked to acquired LQTS in patients treated with an anti-arrhythmic agent. To the best knowledge of the inventor, no one has described diagnosing a predisposition towards an adverse drug or drug-drug reaction which causes QT interval elongation by screening patients for one or more polymorphisms in one or more LQT genes.

1. Cytochrome P450 Genes

The cytochrome P450 enzymes have also been linked to adverse drug reactions. CYP2D6 was the first cytochrome P450 isoform found to be genetically polymorphic in its distribution (Eichelbaum et al., Eur. J. Clin. Pharmacol. 16: 183–7 (1979); and Mahgoub et al., Lancet 2: 584–6 (1977)), and it is now clear that this enzyme metabolizes a large number of drugs (Inaba et al., Can. J. Physiol. Pharmacol. 73: 331–8 (1995); and Buchert et al., Pharmacogenetics 2: 2–11 (1992)). At least 30 mutations exist which alter the activity or specificity of CYP2D6 (Jordan et al., Endocr. Rev. 20: 253–78 (1999)). These include alleles that contain single point mutations resulting in no activity (e.g., CYP2D6*4), alleles in which the CYP2D6 gene has been deleted (e.g., CYP2D6*5) and alleles in which it has been duplicated (e.g., CYP2D6*2_n) (Aklillu et al., J. Pharmacol. Exp. Ther. 278: 441–6 (1996)).

There are numerous cytochrome P450 genes which are involved in the metabolism of drugs and drug metabolites. Several of them include CYP1A2, CYP2C19, CYP2C9, CYP2D6, CYP2E1, CYP3A4, CYP3A5 and CYP3A7. Allelic variations exist amongst these genes. Certain of these allelic variations combine to produce a poor metabolizer phenotype in 7% of Caucasians, but smaller percentages of Africans and Asians and the "ultrarapid" phenotype in ~5% of Caucasian and up to 30% Africans. As ethnic-specific alleles for both Asians (Yokoi et al., Pharm. Res. 15: 517–24 (1998)) and Africans (Aklillu et al., J. Pharmacol. Exp. Ther. 278: 441–6 (1996); and Oscarson et al., Mol. Pharmacol. 52: 1034–40 (1997)) have been identified, that may alter the mean activity of the enzymes in these populations (see Table 1 below), it is also important to test for these alleles in studies of the relationship between genotype and phenotype.

TABLE 1

| Chromosome Distribution of Cytochrome P450 Gene | | | | |
|---|---|---|---|---|
| Chr. 15 | Chr. 10 Polymorphic | Chr. 10 Polymorphic | Chr. 22 Polymorphic | Chr. 10 Chr. 7 |
| | 3–5% Caucasian PMs 15–20% Asian PMs | 1–3% Caucasian PMs | 5–10% Caucasian PMs | |

In fact, due to the metabolic differences, methods have been reported which identify a drug which interacts with the CYP2C19 gene product, S-mephenytoin 4'-hydroxylase (U.S. Pat. No. 5,786,191).

Methods for detecting the presence or absence of mutations in certain of the cytochrome P450 genes have been described. For example, U.S. Pat. No. 5,891,633 relates to a method of identifying mutations in the cytochrome P450 genes CYP2C9 and CYP2A6.

International PCT Application WO 95/30772 reportedly describes a CYP2D6 gene polymorphisms involving a 9 bp insertion in exon 9, which is associated with a slower than normal rate of drug metabolism in individuals bearing it and may be therefore useful diagnostically. PCR primers have been described for detecting mutations in drug metabolism enzymes, including detection of the debrisoquine polymorphism, mephenytoin polymorphism and the acetylation polymorphism (U.S. Pat. Nos. 5,648,484 and 5,844,108). Additional mutations have been identified in CYP2D6 bufuralol-1'-hydroxylase, including mutations at positions 271, 281, 294, and 506 which result in metabolizer/poor metabolizer phenotypes as described in International PCT Application WO 91/10745 and U.S. Pat. No. 5,981,174.

Japanese Patent No. 8168400 provides a method of determining mutations in exons 6 and 7 of the CYP2C19 gene. Japanese Patent No. 10014585 describes primers and methods of detecting a mutation in exon 5 of CYP2C19, which is related to the abnormal metabolism of diazepam, imipramine, omeprazole and propranolol. U.S. Pat. No. 5,912,120 claims a method of diagnosing a patient having a deficiency in S-mephenytoin 4'-hydroxylase activity by detecting polymorphisms at nucleotides 681 or 636.

U.S. Pat. No. 5,719,026 provides methods and primers for detecting a polymorphisms in CYP1A2 and assessing the changes in the drug activity of theophylline associated with those polymorphisms.

Japanese Patent No. 10286090 reportedly describes methods and primers to detect mutations in CYP2E1. These mutations are reported as being useful for determining the safety margin for drug administration for the treatment or related diseases.

Despite these teachings and to the best of the inventor's knowledge, no one has described or suggested that a combination of polymorphisms in LQT and cytochrome P450 genes can induce acquired LQTS in a subject in response to the administration of a drug or drugs.

C. P-glycoprotein Pump Genes

P-Glycoprotein Pump (P-gp) in the development of drug-resistant tumor cells has been extensively studied (Lo et al., *J. Clin. Pharmacol.* 39: 995–1005 (1999)). P-gp is an ATP-dependent drug pump that extrudes a broad range of cytotoxic agents from the cells end is encoded by a gene called MDR-1, for multidrug resistance (Loo et al., *Biochem. Cell. Biol.* 77: 11–23 (1999); and Robert, *Eur. J. Clin. Invest.* 29: 536–45 (1999)). The human P-gp sequence has been described by Chen et al., *Cell* 47: 381–9 (1986) and has the GenBank Accession No. M14758.

Its physiological role may be to protect the body from endogenous and exogenous cytotoxic agents. The protein has clinical importance because it contributes to the phenomenon of multidrug resistance during chemotherapy (Loo et al., 1999) and the development of simultaneous resistance to multiple cytotoxic drugs in cancer cells (Ambudkar et al., *Annu. Rev. Pharmacol. Toxicol.* 39: 361–98 (1999)). Specifically, the over expression of this membrane pump appears to extrude many xenobiotics out of the tumor cells (Robert, 1999). However, considerable controversy remains about the mechanism of action of this efflux pump and its function in normal cells (Ambudkar et al., 1999).

Multidrug resistance (MDR) can be diagnosed in tumors using molecular biology techniques (e.g., gene expression at the mRNA level), by immunological techniques (e.g., quantification of the P-glycoprotein itself) or by functional approaches (e.g., measuring dye exclusion) (Robert, 1999).

Drugs have been developed which reverse or modulate MDR. For example, PSC-833 is a non-immunosuppressive cyclosporin derivative that potently and specifically inhibits P-gp (Atadja et al., *Cancer Metastasis Rev.* 17: 163–8 (1998)). Also, compounds have been identified which increase or modulate the bioavailability of pharmaceutical compounds. See, e.g., U.S. Pat. Nos. 6,004,927; 5,962,522; 5,916,566; 5,716,928; 5,665,386; and 5,567,592. P-gp activity has been altered by expression of antisense nucleotides specific to MDR-1 (U.S. Pat. No. 6,001,991). Methods and assays have also been developed which assess whether multidrug resistance has been reversed (U.S. Pat. No. 5,403,574).

Mutations have also been identified which alter an agents interaction with P-gp. For instance U.S. Pat. No. 5,830,697 discloses single and double mutations (Phe335 and/or 336) which alters the spectrum of cross-reactivity to cytotoxins and resistance to modulation by cyclosporins. Another mutation at V185G in P-gp confers increased resistence to colchicine (U.S. Pat. No. 5,830,697). P-gp sensitivity to vinblastine, colchicine, VP16 and adriamycin, common chemotherapeutic agents, was up- and down-regulated by altering $^{61}$His to another amino acid residue (Taguchi et al., *Biochemistry* 36: 8883–9 (1997)). Moreover, different drugs interact differently with P-gp and mutated forms of P-gp, such that one mutation may influence the activity of one drug and not another (See, e.g., Chen et al., *J. Biol. Chem.* 272: 5974–82 (1997); Bakos et al., *Biochem. J.* 323: 777–83 (1997); and Gros et al., *Proc. Natl. Acad. Sci. USA* 88: 7289–93 (1991)). However, despite the information regarding the influence such mutations may have on drug activity, no association has been made linking P-gp by itself or in combination with another protein in influencing QT intervals or inducing Torsades de Pointes.

II. Nucleic Acid Hybridization

The capacity of a nucleic acid "probe" molecule to hybridize (i.e., base pair) to a complementary nucleic acid "target" molecule forms the cornerstone for a wide array of diagnostic and therapeutic procedures Hybridization assays are extensively used in molecular biology and medicine. Methods of performing such hybridization reactions are disclosed by, for example, SAMBROOOK ET AL., MOLECULAR CLONING: A LABORATORY MANUAL (Cold Spring Harbor Laboratory Press, Cold Spring Harbor, N.Y. (1989)), HAYMES ET AL., NUCLEIC ACID HYBRIDIZATION: A PRACTICAL APPROACH (IRL Press, Washington, D.C. (1985)) and KELLER ET AL., DNA PROBES (2$^{nd}$ Ed., Stockton Press, New York (1993)).

Many hybridization assays require the immobilization of one component to a solid support. Nagata et al., *FEBS Letters* 183: 379–82 (1985) described a method for quantifying DNA which involved binding unknown amounts of cloned DNA to microtiter wells in the presence of 0.1 M MgCl$_2$. A complementary biotinylated probe was then hybridized to the DNA in each well and the bound probe measured colorimetrically. Dahlen et al., *Mol. Cell. Probes* 1: 159–168 (1987) have discussed sandwich hybridization in microtiter wells using cloned capture DNA adsorbed to the wells. An assay for detecting HIV-1 DNA using PCR amplification and capture hybridization in microliter wells also has been reported (Keller et al., *J. Clin. Microbial.* 29: 638–41 (1991)). The NaCl-mediated binding of oligomers to polystyrene wells has been discussed by Cros et al. (French Patent No. 2,663,040) and by Nikiforov et al., *PCR Methods Applic.* 3: 285–291 (1994). A cationic detergent-mediated binding of oligomers to polystyrene wells has been described by Nikiforov et al., *Nucleic Acids Res.* 22: 4167–75 (1994).

III. Analysis of Single Nucleotide DNA Polymorphisms

Many genetic diseases and traits (i.e. hemophilia, sickle-cell anemia, cystic fibrosis, etc.) reflect the consequences of mutations that have arisen in the genomes of some members of a species through mutation or evolution (Gusella, *Ann. Rev. Biochem.* 55: 831–54 (1986)). In some cases, such polymorphisms are linked to a genetic locus responsible for the disease or trait; in other cases, the polymorphisms are the determinative characteristic of the condition.

Single nucleotide polymorphisms (SNPs) differ significantly from the variable nucleotide type polymorphisms (VNTRs), that arise from spontaneous tandem duplications of di- or tri-nucleotide repeated motifs of nucleotides (Weber, U.S. Pat. No. 5,075,217; Armour et al., *FEBS Lett.* 307: 113–5 (1992); Horn et al., PCT Application No. WO 91/14003; Moore et al., *Genomics* 10: 654–60 (1991); Hillel et al., *Genet.* 124: 783–9 (1990)), and from the restriction fragment length polymorphisms ("RFLPs") that comprise variations which alter the lengths of the fragments that are generated by restriction endonuclease cleavage (e.g., Fischer et al., (PCT Application No. WO 90/13668); and Uhlen (PCT Application No. WO 90/11369)).

Because SNPs constitute sites of variation flanked by regions of invariant sequence, their analysis requires no more than the determination of the identity of the single nucleotide present at the site of variation; it is unnecessary to determine a complete gene sequence for each patient. Several methods have been developed to facilitate the analysis of such single nucleotide polymorphisms.

Mundy, C. R. (U.S. Pat. No. 4,656,127), for example, discusses a method for determining the identity of the nucleotide present at a particular polymorphic site that employs a specialized exonuclease-resistant nucleotide derivative.

Cohen et al. (French Patent 2,650,840; and PCT Application No. WO 91/02087) discuss a solution-based method for determining the identity of the nucleotide of a polymorphic site. As in the Mundy method of U.S. Pat. No. 4,656,127, a primer is employed that is complementary to allelic sequences immediately 3' to a polymorphic site.

Additional SNP detection methods include the Genetic Bit Analysis method described by Goelet et al. (PCT Application No. 92/15712). The method of Goelet et al. uses mixtures of labeled terminators and a primer that is complementary to the sequence 3' to a polymorphic site.

Cheesman (U.S. Pat. No. 5,302,509) describes a method for sequencing a single stranded DNA molecule using fluorescently labeled 3'-blocked nucleotide triphosphates. An apparatus for the separation, concentration and detection of a DNA molecule in a liquid sample has been described by Ritterband et al. (PCT Patent Application No. WO 95/17676).

Several primer-guided nucleotide incorporation procedures for assaying polymorphic sites in DNA have been described (Prezant et al., *Hum. Mutat.* 1: 159–64 (1992); Ugozzoli et al., *GATA* 9: 107–12 (1992); and Nyren et al., *Anal. Biochem.* 208: 171–5 (1993)).

IV. Methods of Immobilization Nucleic Acids to a Solid-Phase

Several of the above-described methods involve procedures in which one or more of the nucleic acid reactants are immobilized to a solid support. Currently, 96-well polystyrene plates are widely used in solid-phase immunoassays. PCR product detection methods that use plates as a solid support and DNA chips have been described. The microtiter plate method requires the immobilization of a suitable oligonucleotide probe into the microtiter wells, followed by the capture of the PCR product by hybridization and colorimetric detection of a suitable hapten.

Covalent disulfide bonds have been previously used to immobilize both proteins and oligonucleotides. Chu et al. (*Nucl. Acids Res.* 16: 3671–91 (1988)) discloses a method for coupling oligonucleotides to nucleic acids or proteins via cleavable disulfide bonds.

Gentalen et al., *Nucl. Acids Res.* 27: 1485–91 (1999) describe a cooperative hybridization method lo establish physical linkage between two loci on a DNA strand by using hybridization to a new type of high-density oligonucleotide array. This same method can be used to determine SNP haplotypes.

Yershov et al., *Proc. Natl. Acad. Sci. USA* 93: 4913–8 (1996) describe an oligonucleotide microchip which has been used to detect beta-thalassemia mutations in patients by hybridizing PCR-amplified DNA with the microchips. This technology was suggested for large scale diagnostics in gene polymorphism studies.

Guo et al., *Nucl Acids Res.* 22: 5456–65 (1994) describe a simple method for the analysis of genetic polymorphisms allele-specific oligonucleotide raised bound to glass supports. This method was demonstrated in parallel analysis of 5 point mutations from exon 4 of the human tyrosinase gene.

More recently. Gilles et al., *Nat. Biotechnol.* 17: 365–70 (1999) have described a rapid assay for SNP detection utilizing electronics circuitry on silicon Microchips. Holloway et al., *Hum. Mutat.* 14: 340–7 (1999) also compares methods for high-throughput SNP typing using TaqMan® liquid phase hybridization, PCR-SSOP or ARMS-microplate array diagonal gel electrophoresis (MADGE).

As the world population ages and new drugs are identified, more and more patients will administer one or more pharmaceutical compositions, such that an individual drug or drugs combination can cause adverse drug reactions. Therefore, not withstanding what has been previously reported in the literature, the inventor herein describes methods and compositions for diagnosing drug interactions which involve at least one mutation in a LQT gene. Additional mutations may exist in certain cytochrome 450 genes and P-glycoprotein pumps, which work in concert with a LQT gene mutation or other ion channel (e.g., $K^+$ or $Na^+$) gene polymorphisms to produce an adverse drug or drug-drug reaction. The specification also discloses kits and compositions for diagnosing a subject's predisposition to QT interval elongation in response to the administration of one or more pharmaceutical agents.

SUMMARY OF THE INVENTION

It is an object of the invention to provide novel and improved methods for determining whether a subject has a predisposition for QT interval elongation or Torsades de Pointes due to one or more pharmaceutical agents. The methods comprise the step of screening a biological sample from the subject through a nucleic acid array, wherein said nucleic acid array contains probes for at least two genetic mutations or polymorphisms. These two genetic mutations or polymorphisms are located in two or more of the group of genes consisting of (1) LQT genes, (2) altered sensitivity genes, and (3) increased exposure genes. Preferred genes include LQT genes and MDR genes (e.g., MDR-1). The nucleic acid array can be in the form of a chip, a microchip, a bead or a microsphere. The LQT gene which may contain a polymorphism which induces QT internal elongation include LQT1, LQT2, LQT3, LQT4, LQT5 and LQT6.

The method may further comprise screening both LQT and increased exposure gene (e.g., cytochrome P450 genes) mutations and polymorphism. The P450 cytochrome isoforms which may contain a mutation which can result in excessive accumulation of drugs and thereby induce QT interval elongation include: CYP1A2, CYP2C19, CYP2C9, CYP2D6, CYP2E1, CYP3A, CYP3A5 and CYP3A7.

A further object of the invention is to provide a method for determining whether a subject has a predisposition for QT interval elongation (e.g., acquired LQTS) when treated with one or more pharmaceutical agents comprising the step of screening a biological sample from the subject through a nucleic acid array, such as a DNA array. The DNA array contains probes for two or more genetic mutations or polymorphisms in at least two or more groups of genes wherein the genes are selected from the group consisting of (1) LQT genes, (2) altered sensitivity genes (e.g., MiRP-1genes and its related genes), and (3) increased exposure genes (e.g., multidrug resistant genes and cytochrome P450 genes). The two or more genetic mutations or polymorphisms are found in these genes as at least one or more genetic mutations or polymorphisms in each of the two or more groups of genes. The genes can be selected from those described above.

Another object of the invention is to provide a nucleic acid array comprising nucleic acids which recognize and bind to mutations of the QT syndrome genes (e.g., LQT genes), the altered sensitivity genes (MirR-1 genes) and/or the increased exposure genes.

Another object of the invention is to provide a method of screening one or more pharmaceutical agents in vitro for its or their ability to induce prolonged cardiac repolarization of a cell comprising the steps of A) measuring $I_{Kr}$ and $I_{Ks}$ currents of the cell using a voltage clamp before superfusing the cell with a candidate agent or agents; B) superfusing and incubating the cell with the candidate agent or agents; C) measuring the $I_{Kr}$ and $I_{Ks}$ currents after superfusion and incubation of tie cell with the candidate agent or agents using a voltage clamp; and D) determining whether the $I_{Kr}$ and $I_{Ks}$ currents are inhibited or abolished thereby indicating that the drug prolongs repolarization.

It is another object of the invention to provide a method for identifying genetic polymorphisms and mutations, which can cause QT interval prolongation in a subject comprising the steps of inserting at least two nucleic acids each encoding a polymorphism or mutation of at least two of the following genes: a LQT gene, an altered sensitivity gene, and/or an increased drug exposure gene into a cell; B) measuring $I_{Kr}$ and $I_{Ks}$ currents of the cell before administering a drug known to cause a change in $I_{Kr}$ and/or $I_{Ks}$; C) measuring $I_{Kr}$ and $I_{Ks}$ currents of the cell after superfusion of the cell with the drug; D) comparing the $I_{Kr}$ and $I_{Ks}$ values of the cell expressing the polymorphisms and/or mutations to the $I_{Kr}$ and $I_{Ks}$ values of a cell expressing a wild-type genes; and E) determining if the presence of the polymorphisms and/or mutations leads to greater inhibition or blockage of $I_{Kr}$ and $I_{Ks}$ currents in the cell expressing said polymorphism or polymorphisms.

DETAILED DESCRIPTION OF THE INVENTION

Figure 1:
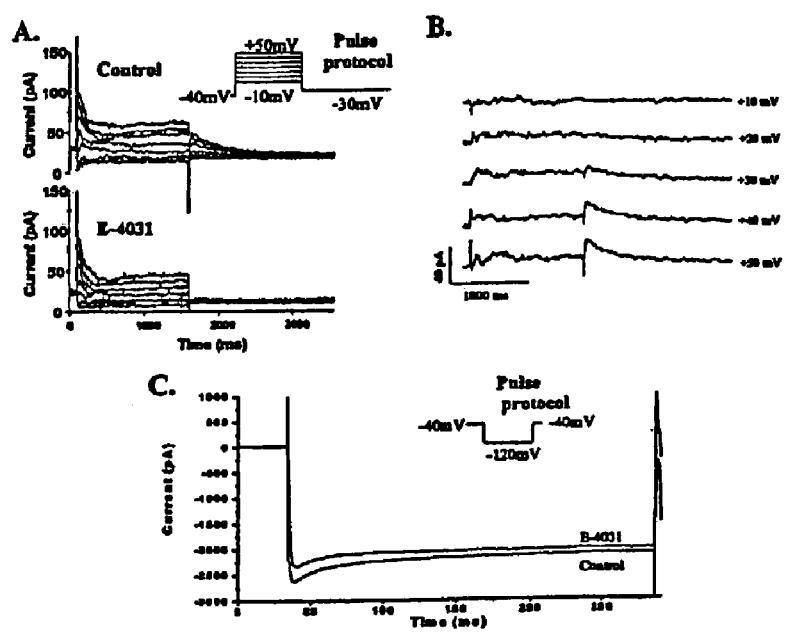
FIG. 1. Recordings of $I_{Kr}$, $I_{to}$ (A and B) and $I_{K1}$ (C) in the same cell before and after 5 minutes superfusion with 5 µmol/L E-4031. Panel A) $I_{Kr}$ and $I_{to}$ currents before and after superfusion with E-4031. E-4031 abolished the $I_{Kr}$ tail current and also reduced the time-dependent $I_{Kr}$ current without affecting the transient outward current ($I_{to}$) or the holding current; Panel B) E-4031 sensitive currents obtained by digital subtraction of currents after E-4031 exposure from currents before E-4031 exposure. Note the inward rectification of the time-dependent $I_{Kr}$ currents at very positive potentials compared with the tail currents; Panel C) $I_{K1}$ current before and after superfusion with E-4031. E-4031 showed little effect on the inward $I_{K1}$ current recorded at −120 mV. The outward holding currents that represent the amplitude of $I_{K1}$ at −40 mV are superimposed.

The invention involves a method for diagnosing a subject's predisposition to an adverse drug response involving a prolonged QT interval, resulting from an excessive accumulation of drugs due to genetic polymorphisms or mutations in at least two classes of genes, which can result in potentially fatal cardiac arrhythmic. The drugs cover an array of pharmaceuticals including anti-arrhythmics, antipsychotics, antidepressants, anti-anginals, antibiotics, antifungals, anti-virals, diuretics, migraine drugs, mental illness therapeutics, breast cancer therapeutics, anxiolytics, antinausea agents, cardiac medication, opiate agonists, antihypertensives, antiinfectives, and anticonvulsants. The inventive method for determining the adverse drug reaction potential utilizes a DNA array (e.g., DNA chip), which can be used to assay a biological sample from a pat example, a patient's DNA sample could be run through a DNA array to diagnose whether the patient has any genetic mutations or polymorphisms that are associated with prolonging cardiac repolarization. Preferred genes, which are associated directly or indirectly with prolonging repolarization, include LQT genes, altered sensitivity genes (e.g., MiRP1 genes or related genes), and increased exposure genes (cytochrome P450 genes and MDR genes).

1. Definitions

By "bp" or "base pair" is meant the hydrogen bonded purine and pyrimidine pair in a double-stranded nucleic acid. Typically in DNA, the pairs are adenine (A) and thiamine (T), and guanine (G) and cytosine (C). In RNA, the pairs are adenine (A) and uracil (U), and guanine (G) and cytosine (C).

By "nucleotide" or "nt" is meant the nucleotide, typically a deoxyribonucleic acid, of the type adenine (A), thiamine (T), guanine (G), uracil (U), and cytosine (C) typically in the sense or coding orientation, but can also include antisense orientations of the gene or coding sequence.

By "nucleic acid" or "nucleic acid molecule" is meant a deoxyribonucleotide or ribonucleotide polymer in either single- or double-stranded form, and unless otherwise limited, would encompass known analogs of natural nucleotides that can function in a similar manner as naturally occurring nucleotides.

By "aa" is meant amino acid.

By "gene" is meant a unit of inheritance that occupies a specific locus on a chromosome (chr.), the existence of which can be confirmed by the occurrence of different allelic forms. Preferred genes of this application are those which impact cardiac repolarization, especially those which act to prolong cardiac repolarization, genes which determine the elimination of drugs from a host, and genes which prolong the time necessary to eliminate a drug from the host. This can include cytochrome P450 genes and ion channel genes.

By "mutation" is meant a one or more nucleotide change in the DNA or RNA sequence of an organism. For example, such mutation can be a frame-shift mutation, a nonsense mutation, or a missense mutation.

By "polymorphism" is meant the existing, in a population, of two or more alleles of a gene, wherein the frequency of the rarer alleles is greater than can be explained by recurrent mutation alone (typically greater than one percent). Said polypmorphisms can consist of one or more nucleotide differences. The polymorphisms can be silent, wherein they do not confer a change in the associated amino acid sequence. Alternatively, the polymorphism can cause an associated change in the amino acid sequence encoded by the gene.

By "altered sensitivity genes" is meant to include genes, which when mutated, alter the expression of proteins which thereupon results in altered sensitivity to a drug or to drugs. Such genes can include for example, the potassium ion channel gene, MiRP1 or related genes.

By "increased exposure gene" is meant to include genes which when aberrantly expressed in a subject lead to increased exposure to a drug or drugs. Such genes can include cytochrome P450 genes, which when mutated lead to decreased or aberrant expression of enzymes required for the elimination of drugs or of a drug. Increased exposure genes also include multidrug resistance (MDR) genes. Mutations in MDR genes can lead to altered distribution (and thereby increased exposure) of a drug or drugs in tissues or in a tissue. MDR genes encode membrane drug transporters and/or ion channel proteins.

By "ion channel gene" is meant to include multidrug resistance genes (MDR genes) as well as ion pump genes such as the LQT family of genes, certain sodium ($Na^+$) channel genes (see, e.g., Chen et al., *Nature* 392: 293–6 (1998)) and certain potassium ($K^+$) channel genes. For example, the potassium ion channel -gene, MiRP1, is one preferred example of a potassium ion channel which may be linked to QT interval prolongation; MiRP1 protein forms channels with HERG and its mutations are associated with cardiac arrhythmia. Preferred MDR genes include MDR-1 which encodes P-glycoprotein pump (P-gp).

By "prolonged QT interval," "QT interval prolongation" or "QT interval elongation" is meant the QT interval measured from QRS onset to T wave offset (QTo) and from QRS onset to T wave peak (QTm) adjusted to a heart rate of 60 beats per minute, which is QTc. By "QTc" is also referred to as the Bazett corrected QT interval. See, e.g., Kligfield et al., *J. Am. Coll. Cardiol.* 28: 1547–55 (1996). Prolonged QT intervals can be induced directly or indirectly by at least two genetic mutations or polymorphism. These mutations or polymorphisms are located in two or more groups of genes (e.g., at least one mutation or polymorphism per gene group), wherein the groups are (1) LQT genes, (2) altered sensitivity genes (e.g., MiRP1 genes), or (3) increased exposure genes (e.g., MDR genes or cytochrome P450 genes).

By "Torsades de Pointes" or "TdP" is an uncommon variant of ventricular tachycardia (VT). The underlying etiology) and management of TdP are, in general, quite different from the more common ventricular tachycardia. TdP is a polymorphous ventricular tachycardia in which the morphology of the QRS complexes vary from beat to beat. The ventricular rate can range from about 150/min to about 250/min. In most cases, there is a constantly changing wave form, but there may not be regularity to the axis changes.

The definition also requires that the Q–T interval be markedly increased (usually to 600 msec or greater). Cases of polymorphic VT, which are not associated with a prolonged Q–T interval, are treated as generic VT. TdP usually occurs in bursts that are not sustained, thus, one usually has a rhythm strip showing the patient's base-line Q–T prolongation By "predisposition" is meant a tendency for a subject to develop TdP de Pointes or QT interval elongation. This tendency may be acquired or hereditary. The preferred subject is a human subject. The predisposition is related to induction of TdP or QT interval elongation upon the administration of one or more pharmaceutical agents which induce TdP or QT interval elongation. These pharmaceutical agents can be those listed herein or any later identified investigational drug which induces QT interval prolongation.

By "LQTS" or "long QT syndrome" is meant a genetic disease which predisposes individuals to ventricular arrhythmia that lead to syncope and sudden death. Congenital or idiopathic LQTS is an inherited form of the disease and is genetically heterogeneous (Wei et al., *Circulation* 92: 1–275 (1995)) and includes the Jervell-Lange-Nielsen and the Romano-Ward-syndromes (Napolitano et al., *Drugs* 47: 51–65 (1994)). Acquired prolonged QT syndromes are largely iatrogenic, and may be induced by certain drugs or associated with metabolic disturbances (e.g., hypokalemia., hypocalcemia or hypomagnesemia) (Napolitano et al., 1994).

By "subject," "patient," or "individual" is meant a mammal, especially a human.

By "nucleic acid array" is meant a substrate to which one or more, preferably 50 or more, more preferably 100–1,000 or more, and more preferably 500 to 5,000 or more nucleic acids are attached. Also, contemplated are arrays with 5,000 to 500,000 nucleic acids attached. One example of such an array is a DNA chip array. For example, see U.S. Pat. Nos. 5,981,956 and 5,922,591. Other examples include Gene Logic's Flow-thru ChipÔ Probe ArraysÔ (U.S. Pat. No. 5,994,068) or the FlowMetrix technology (e.g., microspheres) of Luminex. These arrays are contemplated to contain nucleic acids for wild-type and mutated genes encoding ion channel genes and/or cytochrome P450 genes or isoforms thereof.

By "mutation," "mutant" or "mutated" is meant to refer to a genetic change (e.g., frame-shift mutation, non-sense mutation, missense mutation, deletion, or insertion) in a gene (e.g., ion channel gene, P-gp or a cytochrome P450 gene) resulting in an altered gene expression and/or altered protein function.

By "isoform" is meant different forms of a protein that may be produced from different genes or from the same gene by alternative RNA splicing.

By "binds substantially" is meant to complementary hybridization between an oligonucleotide and a target sequence. By "hybridizing" is meant the binding of two single stranded nucleic acids via complementary base pairing.

The term "primer" refers to an oligonucleotide, whether natural or synthetic capable of acting as a point of initiation of DNA synthesis under conditions in which synthesis of a primer extension product complementary to a nucleic acid strand is induced, i.e., in the presence of four different nucleotide triphosphates and an agent for polymerization (i.e., DNA polymerase or reverse transcriptase) in an appropriate buffer and at a suitable temperature. A primer is preferably a single-stranded oligodeoxyribo-nucleotide. The appropriate length of a primer depends on the intended use of the primer, but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term "primer" may refer to more than one primer, particularly in the case where there is some ambiguity in the information regarding one or both ends of the target region to be amplified. For instance, if a region shows significant levels of polymorphism or mutation in a population, mixtures of primers can be prepared that will amplify alternate sequences. A primer can be labeled, if desired, by incorporating a label delectable by spectroscopic, photochemical, biochemical, immunochemical, or chemical means. For example, useful labels include $^{32}$P, fluorescent dyes, electron-dense reagents, enzymes (as commonly used in an ELISA), biotin, or haptens and proteins for which antisera or monoclonal antibodies are available. A label can also be used to "capture" the primer, so as to facilitate the immobilization of either the primer or a primer extension product, such as amplified DNA, on a solid support.

As used herein and unless described otherwise, "pharmaceutical agent," refers to an agent or drug which alone or in combination with one or more other pharmaceutical agents can induce in a patient prolonged cardiac repolarization. The specific pharmaceutical agents which may induce QT interval elongation are provided herein.

By "$I_{Kr}$" is meant the major rapid repolarizing current in a cell also known as rapid component of the delayed rectifier potassium current. By "$I_{Ks}$" is meant the slower component of the delayed rectifier current. By "$I_{K1}$" is meant inward rectifier current. Both $I_{Kr}$ and $I_{K1}$ are forms of potassium current densities. By "$I_{to}$" is meant the transient outward current of a cell as measured in a voltage clamp assay.

By "biological sample" or "sample" is meant a collection of biological material from a subject containing nucleated cells. This biological material may be solid tissue, for example from a fresh or preserved organ or tissue sample, biopsy or buccal swab; blood or blood constituents; bodily fluids such as amniotic fluid, peritoneal fluid, or interstitial fluid, etc. The sample may contain compounds which are not naturally intermixed with the biological material such as preservatives, anticoagulants, buffers, fixatives, nutrients, antibiotics or the like.

II. Pharmaceutical Agents

One embodiment of the invention is to identify a pharmaceutical agent or combination of agents that induces QT interval elongation in a subject, especially a human. Agents or combinations of agents that induce elongation of the QT interval include, but are not limited to, those listed in Table 2, below. Several of these drugs have been analyzed and have been identified which prolong the QT interval in a concentration-dependent manner (see, e.g., Drici et al., *J. Clin. Psychopharmacol.* 18: 477–81 (1998)).

TABLE 2

Pharmaceutical Agents

| Drug | Brand Name | Drug Class | QT† | TdP† |
|---|---|---|---|---|
| Amiodarone | Cordarone ® | Antiarrhythmic | Yes | Yes |
| Amitriptyline | Elavil ®, Endep ® | Antidepressant | Yes | Yes |
| Amitriptyline HCl-Perphenazine | Etrafon ® | Antidepressant-Antipsychotic | | |
| Amoxapine | Asendin ® | Antidepressant | Yes | |
| Astemizole | Hismanal ® | Antihistamine | Yes | Yes |
| Azelastine | Astelin ® | Antihistamine | Yes | |
| Bepridil | Vascor ® | Antianginal | Yes | Yes |
| Chlorpromazine | Thorazine ® | Mental illness, nausea/vomiting | Yes | Yes |
| Cisapride | Propulsid ® | Stimulates intestinal motility | Yes | Yes |
| Clarithromycin | Abbotic, Biaxin ®, Bicrolid, Clacine, Clambiotic, Claribid, Clarith, Klacid, Klaricid, Klarin, Macladin, Naxy, Veclam | Antibiotic | Yes | |
| Clemastine | Tavist ® | Antihistamine | | Maybe__ |
| Clomipramine | Anafranil ® | Mental illness | Yes | |
| Desipramine | Norpramin ® | Antidepressant | Yes | |
| Diphenhydramine | Benadryl ® | Antihistamine | | Maybe__ |
| Disopyramide‡ | Norpace ® | Antiarrhythmic | Yes | Yes |
| Doxepin | Sinequan ®, Zonalon ® | Antidepressant | Yes | Yes |
| Erythromycin‡ | (Akne-Mycin ®, E.E.S. ®, EryDerm ®, Erygel ®, Ery-Tab ®, Erythrocin ®, Erythromycin Base Filmtab ®, Erythrostatin ®, E-mycin, EryPeds, PCE | Antibiotic and intestinal stimulant | Yes | Yes |
| Felbamate | Felbatrol ® | Anticonvulsant | Yes? | Yes |
| Flecainide | Tambocor ® | Antiarrhythmic | Yes | Yes |
| Fluconazole | Diflucan ® | Antifungal | | |
| Fludrocortisone | Florinef ® | Maintain blood pressure/retain sodium | Yes | |
| Fluoxetine | Prozac ® | Antidepressant | Yes | |
| Fluphenazine | Prolixin ® | Mental illness, Parkinson's Disease | Yes | Yes |
| Fluvoxamine | Luvox ® | Antidepressant | | |
| Foscarnet | Foscavir ® | Antiviral | Yes | |
| Fosphenytoin | Cerebyx ® | Hydanloin | Yes | |
| Halofantrine‡ | | Antimalarial | Yes | Yes |
| Haloperidol | Haldol ® | Mental illness, agitation | Yes | Yes |
| Ibutilide‡ | Corvert ® | Antiarrhythmic | Yes | Yes |
| Imipramine | Tofranil ® | Antidepressant | Yes | |
| Indapamide | Lozol ® | Diuretic | Yes | Maybe__ |
| Isradipine | Dynacirc ® | Cardiac Drug | Yes | |
| Itraconazole | Sporanox ® | Antifungal, Antibiotic | | |
| Ketoconazole | Nizoral ® | Antifungal | | |
| Levomethadyl | Orlaam ® | Opiate agonist | Yes | |
| Maprotiline | Ludiomil ® | Antidepressant | Yes | Yes |
| Moexipril/HCTZ | Uniretic ® | Antihypertensive | Yes | |
| Moricizine | Ethmozine ® | Antiarrhythmic | | Yes |
| Naratriptan | Amerge ® | Migraine therapy | Yes | |
| Nicardipine | Cardene ® | Cardiac drug | Yes | |
| Nortriptyline | Pamelor ®, Aventyl ® | Antidepressant | Yes | |
| Octreotide | Sandostatin ® | Unclassified | Yes | |
| Pentamidine‡ | Pentacarinat ®, Pentam ®, NebuPent ® | Antiinfective | Yes | Yes |
| Perphenazine | Trilafon ® | Mental illness | Yes | Yes |
| Pimozide‡ | Orap ® | Tourette's syndrome, seizures | Yes | Yes |
| Probucol‡ | Lorelco ® | Lowers cholesterol | Yes | Yes |
| Procainamide | Procan ®, Procanbid ®, Pronestyl ® | Antiarrhythmic | Yes | Yes |
| Prochlorperazine | Compazine ® | Nausea | | Maybe__ |
| Protriptyline | Vivactil ® | Antidepressant | Yes | |
| Quetiapine | Seroquel ® | Antipsychotic | Yes | |

TABLE 2-continued

Pharmaceutical Agents

| Drug | Brand Name | Drug Class | QT[†] | TdP[†] |
|---|---|---|---|---|
| Quinidine[‡] | Cardioquin ®, Duraquin ®, Quinidex ®, Quinaglute ® | Antiarrhythmic | Yes | Yes |
| Risperidone | Risperdal ® | Mental illness | Yes | Yes |
| Salmeterol | Serevent ® | Sympathomimetic-Adrenergic | Yes | |
| Sotalol[‡] | Betapace ® | Antiarrhythmic | Yes | Yes |
| Sparfloxacin | Zagam ® | Antibiotic (pneumonia and bronchitis) | Yes | Yes |
| Sumatriptan | Immitrex ® | Migraine treatment | Yes | |
| Tamoxifen | Nolvadex ® | Breast cancer therapeutic | Yes | |
| Terfenadine[‡] | Seldane ® | Antihistamine | Yes | Yes |
| Thioridazine | Mellaril ® | Mental illness | Yes | Yes |
| Thiothixene | Navane ® | Mental illness | Yes | Yes |
| Tizanidine | Zanaflex ® | Muscle relaxant | Yes | |
| Tocainide | Tonocard ® | Antiarrhythmic | Yes | |
| Trifluoperazine | Stelazine ® | Mental illness | Yes | Yes |
| Trimethoprim Sulfamethoxazole | Bactrim ®, Septra ®, Trimeth-Sulfa ® | Antibiotic | | Maybe_ |
| Venlafaxine | Effexor ® | Antidepressant | Yes | |
| Zolmitriptan | Zomig ® | Migraine Treatment | Yes | |

[†]The designation "QT" indicates that QT prolongation is mentioned in the drug's labeling as a potential action of the drug. The designation "TdP" indicates that the FDA has concluded that there is a risk of the drug inducing the syndrome of Torsades de Pointes.
_There are reports in the medical literature that the drug may cause Torsades de Pointes, but the FDA has not stated that the drug may induce TdP.
[‡]For these drugs, women appear to be at greater risk for TdP than men (usually two-fold).

In addition to adverse reactions in a subject to a single pharmaceutical agent, such as those listed above, certain of these agents may induce adverse reactions in specific subjects only when combined with one or more other agents. This is due to two or more genetic polymorphisms located in two or more classes of genes. The mutations or polymorphisms would appear in one or more of the genes in two or more of the classes of genes. The classes of genes include (1) LQT genes, (2) altered sensitivity genes and (3) increased exposure genes. For example, the mutations could occur in one LQT gene and one cytochrome P450 gene or in MiRP1 and LQT3. The polymorphisms or mutations generally cause aberrant enzyme activity resulting in an adverse drug reaction either due to altered sensitivity to the drugs or increased exposure to the drugs. Drugs which likely are involved in adverse drug-drug interactions due to polymorphisms in part in the P450 genes are listed in Table 3 below.

TABLE 3

Drug Interactions Induced in part by Cytochrome P450 Genes

| Drug | Brand Name | Interactions[†] | QT | TdP |
|---|---|---|---|---|
| Amiodarone | Cordarone ® | 1A2 Inhibitor<br>2C9 Inhibitor<br>2D6 Inhibitor<br>3A Inhibitor | Yes | Yes |
| Amitriptyline | Elavil ®, Endep ® | 1A2 Substrate<br>2C19 Substrate<br>2C9 Substrate<br>2D6 Substrate | Yes | Yes |
| Astemizole | Hismanal ® | 3A Substrate | Yes | Yes |
| Cisapride | Propulsid ® | 3A Substrate | Yes | Yes |
| Clarithromycin | Abbotic, Biaxin ®, Bicrolid, Clacine, Clambiotic, Claribid, Clarith, Klacid, Klaricid, Klarin, Macladin, Naxy, Veclam | 3A Substrate<br>3A Inhibitor | Yes | |
| Clemastine | Tavist ® | Interactions | | Maybe_ |
| Clomipramine | Anafranil ® | 1A2 Substrate<br>2C19 Substrate<br>2D6 Substrate<br>2D6 Inhibitor | Yes | |

TABLE 3-continued

Drug Interactions Induced in part by Cytochrome P450 Genes

| Drug | Brand Name | Interactions† | QT | TdP |
|---|---|---|---|---|
| Desipramine | Norpramin ® | 2D6 Substrate | Yes | |
| Erythromycin‡ | (Akne-Mycin ®, E.E.S. ®, EryDerm ®, Erygel ®, Ery-Tab ®, Erythrocin ®, Erythromycin Base Filmtab ®, Erythrostatin ®, E-mycin, EryPeds, PCE | 3A Substrate 3A Inhibitor | Yes | Yes |
| Felbamate | Felbatrol ® | 2C19 Inhibitor | Yes | Yes |
| Flecainide | Tambocor ® | 2D6 Substrate | Yes | Yes |
| Fluconazole | Diflucan ® | 2C9 Inhibitor 3A Inbibilor | | |
| Fluoxetine | Prozac ® | 2C9 Substrate 2D6 Substrate 2C19 Inhibitor 2D6 Inhibitor 3A Inhibitor | Yes | |
| Fluphenazine | Prolixin ® | Interactions | Yes | Yes |
| Fluvoxamine | Luvox ® | 1A2 Substrate 2D6 Substrate 1A2 Inhibitor 2C19 Inhibitor 2C9 Inhibitor 3A Inhibitor | | |
| Halofantrine‡ | | 2D6 Inhibitor | Yes | Yes |
| Haloperidol | Haldol ® | 1A2 Substrate 2D6 Substrate 3A Substrate 2D6 Inhibitor | Yes | Yes |
| Imipramine | Tofranil ® | 1A2 Substrate 2C19 Substrate 2D6 Substrate | Yes | |
| Itraconazole | Sporanox ® | 3A Inhibitor | | |
| Ketoconazole | Nizoral ® | 2C19 Inhibitor 3A Inhibitor | | |
| Protriptyline | Vivactil ® | Interactions | Yes | |
| Quinidine‡ | Cardioquin ®, Duraquin ®, Quinidex ®, Quinaglute ® | 3A Substrate 2D6 Inhibitor | Yes | Yes |
| Risperidone | Risperdal ® | 2D6 Substrate | Yes | Yes |
| Tamoxifen | Nolvadex ® | 2C9 Substrate | Yes | |
| Terfenadine‡ | Seldane ® | 3A Substrate | Yes | Yes |
| Thioridazine | Mellaril ® | 2D6 Substrate | Yes | Yes |
| Trimethoprim Sulfamethoxazole | Bactrim ®, Septra ®, Trimeth-Sulfa ® | Potential 2C9 Inhibitor | | Maybe__ |
| Venlafaxine | Effexor ® | 2D6 Substrate | Yes | |

†"Interactions" indicates that there are drug-drug interactions involving this drug. The entry in this column indicates the cytochrome P-450 isoform for which the drug is either a substrate or an inhibitor.

III. Kits and Methods of Diagnosing Patients with a Predisposition for QT Interval Elongation Although more than 120 mutations have been described in patients with LQTS, not all of these mutations cause QT interval prolongation in a subject after the administration of a specific pharmaceutical agent or agents. Some gene mutations responsible for QT interval prolongation in a subject include, but not limited to, those listed in Table 4 below.

TABLE 7

| Gene | aa Position | nt Position | Mutation Type | *Reference[1] |
|---|---|---|---|---|
| CYP2D6* 4 | | $^{1934}$G ® A | Splice site defect | (53)Oscarson et al., Mol. Pharmacol. 52: 1034–40 (1997)); Topic et al., Clin. Chem. Lab. Med. 36: 655–8 (1998) |
| CYP2D6* 10 | | | C188CIT in exon 1 | Someya et al., Psychiatry Clin. Neurosci. 53: 593–7 (1999) |
| CYP2D6* 17/*17 | | $^{1111}$C ® T $^{2938}$C ® T $^{4268}$G ® C | point mutations | Masimirembwa et al., Br. J. Clin. Pharmacol. 42: 713–9 (1996) |
| HERG | 593 | 1778 | point mutation | Benson et al., Circulation 93: 1791–5 (1996) |
| KCNE1 | 76 | 226 | point mutation | Schulze-Bahr et al., Nature Genet. 17: 267–8 (1997) |
| KCNQ1 | 73 | 217 | point mutation | Donger et al., Circulation 96: 2778–81 (1997) |
| KCNQ1 | 95 | 284 | point mutation | Wang et al., Nature Genet. 12: 17–23 (1996) |
| KCNQ1 | 159 | 475 | point mutation | Wang. et al., (1996) |

TABLE 7-continued

| Gene | aa Position | nt Position | Mutation Type | *Reference[1] |
|---|---|---|---|---|
| KCNQ1 | 174 | 521 | point mutation | Donger et al., (1997) |
| KCNQ1 | 210 | 629 | point mutation | Neyroud et al., Eur. J. Hum. Genet. 6: 129–33 (1998) |
| KCNQ1 | 219 | 655 | point mutation | Russell et al., Hum. Molec. Genet. 5: 1319–24 (1996) |
| KCNQ1 | 220 | 659 | point mutation | Donger et al., (1997) |
| KCNQ1 | 246 | 737 | point mutation | Wang. et al., (1996) |
| KCNQ1 | 249 | 746 | point mutation | Donger et al., (1997) |
| KCNQ1 | 460 | 1378 | point mutation | Donger et al., (1997) |
| KCNQ1 | 415 | 1244–1250 | deletion-insertion | Neyroud et al., (1998) |
| SCN5A | 1505–1507 | 4513–4521 | 9 bp deletion | Wang. Hum. Molec. Genet. 4: 1603–7 (1995) |

Nucleic acids which recognize these mutations can be placed in an array on a substrate, such as on a chip (e.g., DNA chip or microchips). These arrays also can be placed on other substrates, such as microtiter plates, beads or microspheres. Methods of linking nucleic acids to suitable substrates and the substrates themselves are described, for example, in U.S. Pat. Nos. 5,981,956; 5,922,591; 5,994,068 (Gene Logic's Flow-thru ChipÔ Probe ArraysÔ); U.S.Pat. Nos. 5,858,659, 5,753,439; 5,837,860 and the FlowMetrix technology (e.g., microspheres) of Luminex (U.S. Pat. Nos. 5,981,180 and 5,736,330).

The nucleic acids that recognize the polymorphisms of the LQT and cytochrome P450 genes preferably can be linked to a single substrate. Alternatively, in the case of microspheres, the substrate may only comprise a single or a few (e.g., 2, 3, 4, 5, or 10) nucleic acids and may be mixed with microspheres comprising different nucleic acids.

There are two preferred methods to make a nucleic acid array. One is to synthesize the specific oligonucleotide sequences directly onto the solid-phase in the desired pattern (Southern et al., Nucl. Acids Res. 22: 1368–73 (1994): Maskos et al., Nucl. Acids Res. 20: 1679–84 (1992); Pease et al., Proc. Natl. Acad. Sci. 91: 5022–6 (1994): and U.S. Pat. No. 5,837,860) and the other is to presynthesize the oligonucleotides in an automated DNA synthesizer and then attach the oligonucleotides onto the solid-phase support at specific locations (Lamture et al., Nucl. Acids Res. 22: 2121–5 (1994) and Smith et al., Nucl. Acids Res. 22: 5456–64 (1994)). In the first method, the efficiency of the coupling step of each base affects the quality and integrity of the nucleic acid molecule array.

A second, more preferred method for nucleic acid array synthesis utilizes an automated DNA synthesizer for DNA synthesis. The controlled chemistry of an automated DNA synthesizer allows for the synthesis of longer, higher quality DNA molecules than is possible with the first method. Also, the nucleic acid molecules synthesized can be purified prior to the coupling step. The nucleic acids can be attached to the substrate as described in U.S. Pat. No. 5,837,860.

A. Hybridization Detection of PCR Products

Thus, for example, covalently immobilized nucleic acid molecules may be used to detect specific PCR products by hybridization where the capture probe is immobilized on the solid phase or substrate (Ranki et al., Gene 21: 77–85 (1983); Keller et al., J. Clin. Microbiol. 29: 638–41 (1991); Urdea et al., Gene 61: 253–64 (1987)). A preferred method would be to prepare a single-stranded PCR product before hybridization. A patient sample that is suspected to contain the target molecule, or an amplification product thereof, would then be exposed to the solid-surface and permitted to hybridize to the bound oligonucleotide.

The methods of the present invention do not require that the target nucleic acid contain only one of its natural two strands. Thus, the methods of the present invention may be practiced on either double-stranded DNA (dsDNA), or on single-stranded DNA (ssDNA) obtained by, for example, alkali treatment of native DNA. The presence of the unused (non-template) strand does not affect the reaction.

Where desired, however, any of a variety of methods can be used to eliminate one of the two natural stands of the target DNA molecule from the reaction. Single-stranded DNA molecules may be produced using the ssDNA bacteriophage, M13 (Messing et al., Meth. Enzymol. 101: 20–78 (1983); see also, SAMBROOK ET AL., MOLECULAR CLONING: A LABORATORY MANUAL (Cold Spring Harbor Laboratory Press, Cold Spring Harbor, N.Y. (1989)).

Several alternative methods can be used to generate single-stranded DNA molecules. For example, Gyllensten et al., Proc. Natl. Acad. Sci. U.S.A. 85: 7652–6 (1988) and Mihovilovic et al., BioTechiques 7: 14–6 (1989) describe a method, termed "asymmetric PCR," in which the standard "PCR" method is conducted using primers that are present in different molar concentrations.

Other methods have also exploited the nuclease resistant properties of phosphorothioate derivatives in order to generate single-stranded DNA molecules (U.S. Pat. No. 4,521, 509); Sayers et al., Nucl. Acids Res. 16: 791–802 (1988); Eckstein et al., Biochemistry 15: 1685–91 (1976); and Ott et al., Biochemistry 26: 8237–41 (1987): and SAMBROOK et al.,1989).

C. Screening Polymorphisms

Screening polymorphisms in samples of genomic material according to the methods of the present invention, is generally carried out using arrays of oligonucleotide probes. These arrays nay generally be "tiled" for a large number of specific polymorphisms. By "tiling" is generally meant the synthesis of a defined set of oligonucleotide probes which is made up of a sequence complementary to the target sequence of interest, as well as preselected variations of that sequence, e.g., substitution of one or more given positions with one or more members of the basic set of monomers. i.e. nucleotides. Tiling strategies are discussed in detail in Published PCT Application No. WO 95/11995, incorporated herein by reference in its entirety for all purposes. By "target sequence" is meant a sequence which has been identified as containing a polymorphism or mutation (e.g., a single-base polymorphism also referred to as a "biallelic base"). It will be understood that the term "target sequence" is intended to encompass the various forms present in a particular sample of genomic material, i.e., both alleles in a diploid genome.

In a particular aspect, arrays are tiled for a number of specific, identified polymorphic marker sequences. In particular, the array is tiled to include a number of detection blocks, each detection block being specific for a specific polymorphic marker or set of polymorphic markers. For example, a detection block may be tiled to include a number of probes which span the sequence segment that includes a specific polymorphism. To ensure probes that are complementary to each variant, the probes are synthesized in pairs differing, for example, at the biallelic base.

In addition to the probes differing at the biallelic bases, monosubstituted probes can be generally tiled within the detection block. These monosubstituted probes have bases al and up to a certain number of bases in either direction from the polymorphisms, substituted with the remaining nucleotides (selected from A, T, G, C or U). Typically, the probes in a tiled detection block will include substitutions of the sequence positions up to and including those that are 5 bases away from the base that corresponds to the polymorphism. Preferably, bases up to and including those in positions 2 bases from the polymorphism will he substituted. The monosubstituted probes provide internal controls for the tiled array, to distinguish actual hybridization from artifactual cross-hybridization.

A variety of tiling configurations may also be employed to ensure optimal discrimination of perfectly hybridizing probes. For example, a detection block may be tiled to provide probes having optimal hybridization intensities with minimal cross-hybridization. For example, where a sequence downstream from a polymorphic base is G–C rich, it could potentially give rise to a higher level of cross-hybridization or "noise," when analyzed. Accordingly, one can tile the detection block to take advantage of more of the upstream sequence.

Optimal tiling configurations may be determined for any particular polymorphism by comparative analysis. For example, triplet or larger detection blocks may be readily employed to select such optimal tiling strategies.

Additionally, arrays will generally be tiled to provide for ease of reading and analysis. For example, the probes tiled within a detection block will generally be arranged so that reading across a detection block the probes are tiled in succession, i.e., progressing along the target sequence one or more nucleotides at a time.

Once an array is appropriately tiled for a given polymorphism or set of polymorphisms (e.g., LQT and cytochrome P450 genes), the target nucleic acid is hybridized with the array and scanned. Hybridization and scanning are generally carried out by methods described in, e.g., PCT Application Nos. WO 92/10092 and WO 95/11995, and U.S. Pat. No. 5,424,186. In brief, a target nucleic acid sequence, which includes one or more previously identified polymorphic markers, is amplified by well known amplification techniques, e.g., polymerase chain reaction (PCR). Typically, this involves the use of primer sequences that are complementary to the two strands of the target sequence both upstream and downstream from the polymorphism. Asymmetric PCR techniques may also be used. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

Although primarily described in terms of a single detection block, e.g., for detection of a single polymorphism, in the preferred aspects, the arrays of the invention will include multiple detection blocks, and thus be capable of analyzing multiple, specific polymorphisms. For example, preferred arrays will generally include from about 50 to about 4,000 different detection blocks with particularly preferred arrays including from 10 to 3,000 different detection blocks.

In alternate arrangements, it will generally be understood that detection blocks may be grouped within a single array or in multiple, separate arrays so that varying, optimal conditions may be used during the hybridization of the target to the array. For example, it may often be desirable to provide for the detection of those polymorphisms that fall within G–C rich stretches of a genomic sequence, separately from those falling in A–T rich segments. This allows for the separate optimization of hybridization conditions for each situation.

Additional methods of detecting gene mutations (e.g., polymorphisms) includes the methods described in International PCT applications WO 99/42622; WO 99/29901; WO 98/49341; WO 97/27317; and W97/22720.

D. Calling

After hybridization and scanning, the hybridization data from the scanned array is then analyzed to identify which variant or variants of the polymorphic marker are present in the sample, or target sequence, as determined from the probes to which the target hybridized, e.g., one of the two homozygote forms or the heterozygote form This determination is termed "calling" the genotype. Calling the genotype is typically a matter of comparing the hybridization data for each potential variant, and based upon that comparison, identifying the actual variant (for homozygotes) or variants (for heterozygote) that are present. In one aspect, this comparison involves taking the ratio of hybridization intensities (corrected for average background levels) for the expected perfectly hybridizing probes for a first variant versus that of the second variant. Where the marker is homologous for the first variant, this ratio will be a large number, theoretically approaching an infinite value. Where homozygous for the second variant, the ratio will be a very low number i.e., theoretically approaching zero. Where the marker is heterozygous, the ratio will be approximately 1. These numbers are, as described, theoretical. Typically, the first ratio will be well in excess of 1, i.e., 2, 4, 5 or greater. Similarly, the second ratio will typically be substantially less than 1, i.e., 0.5, 0.2, 0.1 or less. The ratio for heterozygotes will typically be approximately equal to 1, i.e., from 0.7 to 1.5. These ratios can vary based upon the specific sequence surrounding the polymorphism, and can also be adjusted based upon a standard hybridization with a control sample containing the variants of the polymorphism .

The quality of a given call for a particular genotype may also be checked. For example, the maximum perfect match intensity can be divided by a measure of the background noise (which may be represented by the standard deviation of the mismatched intensities). Where the ratio exceeds some preselected cut-off point, the call is determined to be good. For example, where the maximum intensity of the expected perfect matches exceeds twice the noise level, it might be termed a good call. Further description of software used for genetic calling can be used as described in U.S. Pat. No. 5,858,659.

E. Method of Identifying New Polymorphisms

Another aspect of the invention is to identify polymorphisms or mutations which are associated with or indirectly involved with QT interval prolongation. These polymorphisms or mutations are located in at least two classes of genes (e.g., LQT genes, altered sensitivity genes or increased exposure genes). Moreover, the mutations or polymorphisms can be those which have been previously identified but not linked with QT interval elongation. Alternatively, once new mutations or polymorphisms are identified, these also can be assessed using the assays described herein to determine whether the "new mutation" and/or "polymorphism" can cause QT interval elongation. As new polymorphisms and mutations are identified, the nucleic acids which recognize these polymorphisms can be added to the nucleic acid array for screening subjects. One method of identifying such "new" polymorphisms is to obtain biological samples from subjects who have experienced acquired LQTS due to administration of a drug or drugs and to sequence the LQT genes or P450 genes to isolate the polymorphism which was responsible for the adverse drug reaction.

Alternatively, for known mutations and polymorphisms in each of these gene classes, which previously has not been associated with adverse drug reactions, the drugs can be assessed for their ability to elongate the QT interval as discussed.

IV. Method of Identifying Agents Which Induce Prolonged Repolarization

Methods of identifying agents which prolong QT intervals can be preformed as described in the examples provided below. Alternatively, agents can be assayed using the Langeudorff technique in, for example., isolated perfused rabbit hearts, or the whole-cell patch-clamp technique in ventricular myocytes to examine the TdP difference. Liu et al., *J. Cardiovasc. Pharmacol.* 34: 287–94 (1999) and Ebert et al., *J. Womens Health* 7: 547–57 (1998) used these techniques to examine the gender difference of Torsades de Pointes (TdP) between men and women. Drici et al., *J Cardiovasc. Pharmacol.* 34: 82–8 (1999) used isolated Langendorff-perfused rabbit hearts to lest the effect of the agent, Tegaserod (HTF 919), on cardiac repolarization. Perfused (Langendorff) feline hearts can also be used, as described in Wang et al., *J. Cardiovasc. Pharmacol.* 32: 123–8 (1998), in which the authors used the model system to assess QT prolongation in response to antihistamine administration. The whole-cell patch-clamp technique was utilized to study the effect of tamoxifen on the delayed rectifier ($I_{Kr}$), the inward rectifier ($I_{K1}$) the transient outward current ($I_{to}$) and the inward L-type calcium current ($I_{Ca}$) in rabbit ventricular myocytes (Liu et al., *J. Pharmacol. Exp. Ther.* 287: 877–83 (1998)).

In addition to the above in vitro methods, determination of the effect of a particular compound can also be performed by using an electrocardiogram (ECG) to study the pharmokinetics of a drug's effect on QTC prolongation (see, e.g., Sale et al., *Clin. Pharmacol. Ther.* 56: 295–301 (1994)).

Methods of measuring potassium ($K^+$) currents in AT1 cells and in oocytes are known in the art and can performed using the methods, for example, described by Yang et al., *Circulation* 91: 1799–1806 (1995); and Driga et al., *Biophysics J.* 74: A210 (1998). Basically, the cells are transfected with a nucleic acid with the putative mutation believed to cause QT prolongation when exposed to an agent known to cause QT elongation. The $I_{Kr}$ and $I_{Ks}$ and even the $I_{to}$ responses are measured and compared to a cell expressing the normal wild type gene. This can also be done when testing $Na^+$ current changes.

The effect of the genetic mutations can also be assessed using voltage sensitive dye methods. Assaying changes to cell voltage using dyes are known in the art. See, for example, Morley et al., *J. Cardiovasc. Electrophysiol.* 10: 1361–75 (1999) and Dillon et al., *Science* 214: 453–6 (1981).

The following examples are offered to illustrate embodiments of the invention, and should not be viewed as limiting the scope of the invention.

EXAMPLES

Example 1

Method and Kit for Determining a Subject's Redisposition to Adverse Reactions to Tamoxifen The metabolic pathways of tamoxifen are complex and have been extensively studied. Tamoxifen metabolism involves multiple pathways, and the primary and secondary metabolites have variable pharmacological activities, with certain of the metabolites causing considerable inter-individual variability. In vitro and in vivo studies in humans have shown that the main routes of tamoxifen metabolism include N-demethylation, N-oxidation and 4-hydroxylation (Buckley et al., *Drugs* 37: 451–90 (1989); and Lim et al., *Carcinogenic* 15: 589–93 (1994)). Tamoxifen N-demethylation, which appears quantitatively the most important pathway, is primarily catalyzed by CYP3A (Jacolot et al., *Biochem. Pharmacol.* 41: 1911–9 (1991); (Mani et al., *Drug Metab. Dispos.* 21: 645–56 (1993)). However CYP2D6 also appears to be a major enzyme that catalyzes tamoxifen 4-hydroxylation (Crewe et al., *Biochem. Pharmacol.* 53: 171–8 (1997)).

Methods for DNA extraction. Blood is drawn from a subject, e.g., human, into sodium heparin Vacutainers (Becton Dickinson; Franklin Lakes, N.J.) and then is transferred to Corning 5.0 ml cryogenic vials (Corning; Cambridge, Mass.). The blood is frozen in a non-frost free −20° C. freezer until use.

Reagents, which are used to extract the DNA from whole blood, are the QIAGEN Blood Midi Kit® unless otherwise noted. 200 µl of QIAGEN protease is added to a 15 ml centrifuge tube. The blood is thawed and 2.0 ml added to the tube followed by 2.0 ml of Buffer AL. The tube is capped and contents mixed with a vortexer for 15 seconds. After vortexing, 2 ml of 95% ethanol is added, and the contents mixed by inversion. The contents of the tube is then added to a QIAGEN Midi Spin column that is placed in a collection tube. The column and collection tube are centrifuged at 6,000×g at 4° C. for two minutes. Then the collection tube is discarded and replaced with a new collection tube. Two ml of Buffer AW is added to the spin column, and the column is centrifuged again at 6,000×g at 4° C. for two minutes. The column is rinsed again by discarding the collection tube, replacing it with a new collection tube, adding 2.0 ml of Buffer AW to the spin column, and centrifuging at 6,000×g at 4° C. for two minutes. The used collection tube is discarded and replaced with a new collection tube. The DNA is eluted from the column by adding 1 ml of elution buffer to the spin column, incubating at room temperature for one minutes, and then centrifuging at 6,000×g at 4° C. for two minutes. The DNA is transferred to a Sarstedt 2.0 ml screw-top tube (#72730006, Sarstedt; Newton, N.C.) and frozen at −20° C.

The DNA concentration is measured using the 260/280 method in a spectrophotometer, and the DNA concentration adjusted to 60 ng/µl with water.

DNA from buccal swabs is obtained as follows. Buccal cells are obtained by gently rubbing a sterile cotton swab within the subject's mouth. The swab is placed in a Falcon 2063 tube, and 1.5 mls of 1×PBS is added, mixed, and centrifuged at 3K for 5 minutes to pellet the cells. The supernatant is removed, and this process is repealed with another 1 ml of 1×PBS. The cell pellet is then suspended in 47 µl of PCR lysis buffer (Promega PCR Buffer B and 10 mg/ml Proteinase K). Samples are incubated for 30 minutes at 60° C. and the reaction stopped by boiling the sample for 10 minutes. The sample is then centrifuged at 3K for 5 minutes and stored at −20° C. until use.

CYP2D6 and CYP2C19 Genotyping Using the Affymetrix P450 GeneChip®. Reagents used in this protocol use the Affymetrix P450 GeneChip Kit® unless otherwise noted. The reaction mass mix is prepared in a template free area by combining the following:

TABLE 4

PCR Amplification

| | per reaction | Final concentration |
|---|---|---|
| H$_2$O | 23 μl | |
| Affymetrix CYP450 primer mix | 4 μl | 200 μM |
| 20% DMSO | 5 μl | 2.0% |
| 2.0 mM dNTP mix | 5 μl | 200 μM |
| AmpliTaq Gold ® PCR buffer | 5 μl | 1 X |
| 25 mM MgCl$_2$ | 5 μl | 2.5 mM |
| 5 U/μl AmpliTaq Gold ® Taq polymerase | 1 μl | 5 U |

TABLE 5

Primers

| CYP 2D6 | Upstream Primer | Downstream Primer |
|---|---|---|
| Exon 1/2 | 5'-CAGAGGAGCCCATTTGGTA GTG AGGCAGGT-3' | 5'-GGTCCCACGGAAATCTGTC TCTGT-3' |
| Exon 3/4 | 5'-CACGCGCACGTGCCCGTCC CA-3' | 5'-CTCTCGCTCCGCACCTCGC GCAGA-3' |
| Exon 5/6 | 5'-GGACTCTGTACCTCCTATC CACG TCA-3' | 5'-CCTCGGCCCCTGCACTGTT TCCCA GA-3' |
| Exon 7/7 | 5'-GGCGACCAGAGATGGGTGA CCA GGCTC-3' | 5'-GCGCCAGGCCTACCTTAGG GATG CGGGA-3' |
| Exon 8/9 | 5'-GGGAGACAAACCAGGACCT GC CAGA-3' | 5'-CATCTGCTCAGCCTCAACG TACC CCTGTCT-3' |

The required number of Micro-Amp® 8-strip Reaction Tubes are placed in a 96-well tube/tray retainer and the assembly is placed in a MicroAmp® base (all Perkin-Elmer; Foster City, Calif.). forty-five μl of the mass mix is aliquoted into the 0.2 ml MicroAmp tubes and the tubes are capped. The tubes are then transferred to a medium template area to add the DNA.

Five μl of DNA (60 ng/μl) is added to each sample tube; 5 μl of Affymetrix CYP450 Reference DNA is added to the positive control tube; and 5 μl of water are added to negative control tube. The tubes are then capped, and the rack centrifuged in a table top centrifuge at 2,000 rpm for 1 minute.

The samples are then placed in a Perkin-Elmer Gene-Amp® PCR System 9600 thermocycler programmed for: 95° C. for 5 minutes, then 15 cycles of 95° C./40 seconds, 65° C./50 seconds, 72° C./50 seconds followed by 30 cycles of 95° C./30 seconds, 65° C./50 seconds, 72° C./50 seconds plus one second per cycle then a final extension of 72° C. for 7 minutes.

A 10 μl aliquot of each product is loaded (with loading buffer) onto a 2% agarose. The gel is run until the bromophenol blue band is ⅔ of the way down the gel, and photographed on a UV transilluminator. Correctly amplified products appear as bands of 159, 171, 250, 444, 762, 878 and 1,125 base pairs. All bands must be present to obtain both CYP2D6 and CYP2C19 calls. Failure of the larger two bands to amplify precludes any CYP2D6 call. If all bands are present then the next step is that of fragmentation.

Fragmentation. A clean reaction tube rack is placed on ice with one tube for each sample that is to be fragmented. All fragmentation mass mix reagents are kept on ice, and the mass mix prepared by combining the reagents as directed in Table 7.

TABLE 6

| | 25 μl mass mix | 250 μl mass mix |
|---|---|---|
| Fragmentation reagent | 1 μl | 2 μl |
| 20 mM EDTA | 1 μl | 2 μl |
| 1 U/μl alkaline phosphatase | 12.5 μl | 25 μl |
| water | 110.5 μl | 221 μl |

125 μl mass mix for 1–25 reactions, 250 μl mass mix for 25–50 reactions. Five μl of the fragmentation mass mix is added to each tube (on ice), and 10 μl of PCR product is added to the tubes. The tubes are capped and either the rack tapped against a bench top briefly or quickly centrifuged at 4° C. to bring the components together. The rack is then placed in a Perkin-Elmer GeneAmp® PCR System 9600 thermocycler and the 25° C./20 minutes, 95° C./10 minutes, 4° C. hold fragmentation program is run.

Labeling. The labeling master mix is prepared by combining the reagents in a microcentrifuge tube as follows:

TABLE 7

| | per reaction | Final |
|---|---|---|
| Terminal Transferase Buffer | 4 μl | 1 X |
| Fluorescein N6-ddATP | 0.5 μl | 25 μM |
| 20 U/μl Terminal Transferase | 0.5 μl | 10 U |

Five μl of the labeling master mix is added to each tube of fragmented product, and the rack placed in a Perkin-Elmer GeneAmp® PCR System 9600 thermocycler and the 37° C./35 minutes, 95° C./5 minutes, 4° C. hold labeling program is run.

Hybridization Preparation. The following solutions are prepared according to the direction in the Affymetrix® GeneChip® CYP450 instruction booklet:

Hybridization Concentrate:
  5.5×SSPE, 0.055% Triton® X-100, and 1.1 mM CTAB (hexadecyltrimethylammonium bromide, Sigma H-6269; St. Louis, Mo.)

Hybridization Master Mix:
  Combine 45.5 ml hybridization concentrate, 1 ml molecular biology grade water, 1 ml 50×Denhardt's Solution, and 500 μl Affymetrix® Control Oligonucleotide F1. Place 480 μl aliquots in 1.5 ml Eppendorf Safe-Lock microcentrifuge tubes and freeze at −20° C. (the combination of Denhardt's Solution and CTAB may cause background. If so, substitute molecular biology grade water for the Denhardt's Solution).

Hybridization. Twenty μl of fragmented and labeled PCR product is added to a tube of Hybridization Master Mix and labeled with the sample. The tubes are placed in boiling water for 10 minutes and then immediately transferred to ice. The tubes are kept on ice at least 10 minutes. While the tubes are on ice, the Affymetrix® Fluidics Station is primed with water. Wash Buffer A (3×SSPE, 0.005% Triton X-100 and 1 mM CTAB) and Wash Buffer B (6×SSPE).

A CYP450 Probe array is placed in the Fluidics Station module, and one of the Hybridization Master Mix/DNA tubes placed in the lower compartment. The CYP450 Hybridization protocol is run on the Fluidics Station.

Scanning and Analysis. The hybridized chip is transferred from the Fluidics Station to the Scanner. A scan protocol is then run on the chip as directed by Affymetrix®. After the scan is completed, the Analysis program is run and the report prepared. The results are entered into an appropriate database.

Conventional CYP2D6*4 Assay, Amplification. Five µl of DNA (60 ng/µl) is added to 20 µl of PCR reaction mix containing 1×PCR Buffer B (Promega; Madison, Wis.) [50 mM KCl, 10 mM Tris-HCl (pH 9.0), 1.0% Triton X-100]; 25 pmol of each primer, 200 µM of each dNTP, 1.5 mM $MgCl_2$ and 0.75 U of Taq polymerase (Promega; Madison, Wis.) in 500 µl PCR reaction tubes. Twenty five µl of mineral oil is added to the top of each reaction tube. The primers used are those of Heim et al., *Metho. Enzymol.* 206 :173–83 (1991): 5'-TGC CGC CTT CGC CAA CCA CT-3' (SEQ ID NO: 11) upstream and 5'-GTG CGG AGC GAG AGA CCG AGG-3' (SEQ ID NO: 12) downstream. The tubes are briefly centrifuged in a microcentrifuge and placed in a Perkin Elmer® model 480 thermocycler. The amplification program used is 2 minutes at 94° C. denaturation; 35 cycles of 1 minute at 94° C.; 1 minute at 63° C.; 1 minute at 72° C.; with a final extension of 4 minutes at 72° C.

Restriction Enzyme Digestion. A mass mix containing 2 µl of BstNI (NEB; Beverly, Mass.), 3 µl of NEB Buffer 2, and 0.3 µl of 100×BSA per reaction is prepared and 5.3 µl added to each reaction tube. The tubes are briefly centrifuged in a microcentrifuge to bring the restriction enzyme mix below the mineral oil and incubated at 60° C. for at least four hours.

Gel Electrophoresis. The samples are electrophoresed on a 2.0% agarose gel. Wild-type allele produces 110 and 182 base pair fragments. The *4 mutant produces a 292 base pair fragment and a heterozygote shows 110, 182 and 292 base pair bands on the gel.

Conventional CYP2D6*10 Assay.

Amplification. The assay that is used for CYP2D6*10 is a two amplification allele specific oligonucleotide method.

Amplification 1. Five µl of DNA (60 ng/ µl) is added to 45 µl PCR reaction mix containing 1×PCR buffer B (Promega; Madison, Wis.) [50 mM KCl, 10 mM Tris-HCl (pH 9.0), 1.0% Triton X-100]; 25 pmol of each primer, 200 µM of each dNTP, 1.0mM $MgCl_2$ and 0.75 U of Taq polymerase (Promega, Madison, Wis.) in 200 µl PCR tube strips. The primers used are: 5'-ACC AGG CCC CTC CAC CGG-3' upstream (primer 9) (SEQ ID NO: 13) and 5'-TCT GGT AGG GGA GCC TCA GC-3' downstream (primer 10) (SEQ ID NO: 14). The tube rack is briefly centrifuged in a table top centrifuge and placed in a Perkin Elmer® model 9600 thermocycler programmed to run 4 minutes at 94° C. denaturation; 35 cycles of 1 minute at 94° C.; 1 minute at 58° C., 1 minute at 72° C., with a final extension of 4 minutes at 72° C. program.

Amplification 2. Two mass mixes are made for each sample. The wild-type mass mix contains primers 9 and 11 (primer 11 is 5'-CCA CCA GGC CCC CT-3' (SEQ ID NO: 15) and the mutant mass mix contains primers 9 and 12 (5'-GCA CCA GGC CCC GT-3') (SEQ ID NO: 16). With both mass mixes, 3 µl of product from the first amplification is added to 47 µl of PCR reaction mix containing 1×PCR buffer B (Promega; Madison, Wis.) [50 mM KCl, 10 mM Tris-HCl (pH 9.0), 1.0% Triton X-100]; 25 pmol of each primer, 200 µM of each dNTP, 1.0 mM MgCl2 and 0. 75 U of Taq polymerase (Promega; Madison, Wis.) in 200 µl PCR tube strips. The tube rack is briefly centrifuged in a tabletop centrifuge and placed in a Perkin Elmer® model 9600 thermocycler which is programmed to run the 4 minutes at 94° C. denaturation; 35 cycles of 1 minute at 94° C.; 1 minute at 52° C.; 1 minute at 72° C.; with a final extension of 4 minutes at 72° C. programmed.

Gel Electrophoresis. The samples are electrophoresed in pairs (wild type and mutant) on a 2.0% agarose gel. Wild-type allele produces a 516 bp product only with the wild type reaction mix. The *10 mutant allele produces a 516 bp product only with the mutant reaction mix. A heterozygote produces product with both mixes.

Conventional CYP2C9 144 Assay, Amplification. Fife µl of DNA (60 ng/µl) is added to 20 µl of a PCR reaction mix containing 1×PCR buffer B (Promega; Madison, [50 mM KCl, 10 mM Tric-HCl (pH 9.0), 1.0% Triton X-100]; 25 pmol of each primer, 200 µM of each dNTP, 1.0 mM $MgCl_2$ and 0.75 U of Taq polymerase (Promega; Madison, Wis.) in 500 µl PCR reaction tubes. Twenty five µl of mineral oil is added to the top of each of the reaction tubes. The primers used are those of Bhasker et al., *Pharmacogenetics* 7: 51–8 (1997); 5'-TTC TCA AAA GTC TAT GGT-3'upstream (SEQ ID NO: 17) and 5'-GCC TTG TGG AGG AGT TGA-3'downstream (SEQ ID NO: 18). The tubes are briefly centrifuged in a microcentrifuge and placed in a Perkin Elmer® model 480 thermocycler. The amplification program used is 2 minutes at 94° C. denaturation; 35 cycles of 1 minute at 94° C.; 1 minute at 50° C.; 1 minute at 720C.; with a final extension of 4 minutes at 72° C.

Restriction Enzyme Digestion. A mass mix containing 2 µl of Ava II (New England Biolabs, NEB; Beverly, Mass.) and 3 µl of NEB Buffer, 4 per reaction, is prepared, 5 µl is added to each reaction tube. The tubes are centrifuged briefly in a microcentrifuge to bring the restriction enzyme mix below the mineral oil layer and incubated at 37° C. for at four hours.

Gel Electrophoresis. The samples are electrophoresed on a 2.0% agarose gel. Wild-type allele produces 44 and 256 base pair fragments. The 144 mutant produces a 349 base pair (bp) fragment; and a heterozygote shows 44, 256 and 349 bp bands on the gel.

Conventional CYP2C9 358 Assay.

Amplification. Five µl of DNA (60ng/µl) is added to 20 µl of a PCR reaction mix containing 1×PCR buffer B (Promega; Madison, Wis.) [50 mM KCl, 10 mM Tris-HCl (pH 9.0), 1.0% Triton X-100]; 25 pmol of each primer, 200 µM of each dNTP, 1.5 mM $MgCl_2$ and 0.75 U of Taq polymerase (Promega; Madison, Wis.) in 500 µl PCR reaction tubes. 25 µl of mineral oil is added to the top of each of the reaction tubes. The primers used are those of Bhasker et al. *Pharmacogenetics* 7 : 51–8 (1997); 5'-GTC CAG GAA GAG ATT GAT C-3' upstream (SEQ ID NO: 19) and 5'-CAG AAA CTA CCT CAT CCC CAA-3' downstream (SEQ ID NO: 20). The tubes are briefly centrifuged in a microcentrifuge and placed in a Perkin-Elmer model 480 thermocycler. The amplification program used is 2 min. at 94° C. denaturation; 35 cycles of 1 min. at 94° C.; 1 min. at 50° C.; 1 min. at 72° C.; with a final extension of 4 mm. at 72° C.

Restriction Enzyme Digestion. A mass mix containing 2 µl of Nsi I (NEB; Beverly, Mass.) and 3 µl of NEB Nsi I Buffer per reaction is prepared, and 5 µl added to each reaction tube. The tubes are centrifuged briefly in a microcentrifuge to bring the restriction enzyme mix below the mineral oil layer and incubated for 4 hrs. at 37° C.

Gel Electrophoresis. The samples are electrophoresed on a 2.0% agarose gel. Wild-type allele produces a 181 bp fragment. The 358 mutant produces 73 and 108 bp fragments. A heterozygote appears with 73, 108 and 181 bp bands on the gel.

Example 2

In vitro Model to Study Tamoxifen $I_{Kr}$ is one of the major polarizing currents and its block has been implicated in TdP (Carlsson et al., *J. Cardiovasc. Pharmacol.* 16: 276–85 (1990); Roden et al., *Am. Hear. J.* 111: 1088–93 (1986); Woosley, *Annu. Rev. Pharmacol. Toxicol.* 36: 233–52 (1996); and Follmer et al., *Circulation* 82: 289–93 (1990)). To evaluate whether tamoxifen affects $I_{Kr}$, we first establish the presence of $I_{Kr}$ in the chosen model, rabbit ventricular myocytes, using a drug known to be specific for blocker of $I_{Kr}$. Other suitable models, such as feline myocytes or HEK293 cells expressing HERG, can be substituted for rabbit myocytes. FIGS. 1A and 1B show the membrane currents elicited by a 1.5-second voltage-clamp step from −40 mV to different test potentials ranging from −10 to −50 mV in the same cell before (Panel A) and after (Panel B) 5 minutes exposure to 5 μmol/L E-4031, a highly selective $I_{Kr}$ blocker (Clay et al., *Biophys J.* 69: 1830–7 (1995); and Sanguinetti et al., *J. Gen. Physiol.* 961: 195–215 (1990)). Under control conditions, a relatively slowly activating outward current flowed during depolarization, followed by an outward tail current that has been shown to represent the gradual decay of $I_{Kr}$ (Follmer et al., *Circulation* 82: 289–93 (1990); Clay et al., (1995); and Sanguinetti et al., (1990)). The initial peak in the time-dependent outward current was due to the rapid activation and inactivation of $I_{to}$, which is sensitive to 4-aminopyridine. E-4031 abolished the tail current upon repolarization and also reduced the time-dependent outward current, without affecting the initial peak ($I_{to}$) or the holding current ($I_{K1}$). Shown in Panel B are the E-4031 sensitive currents obtained by digital subtraction of currents in the bottom tracings from currents in the top tracings in panel A. Compared with the tail current, the time-dependent current demonstrated marked inward rectification at very positive potentials, $I_{to}$ was not present in the E-4031 sensitive currents, indicating E-4031 has no effect on $I_{to}$ at this concentration. Superfusion with 1–2.5 μmol/L dofetilide or removal of extracellular K$^+$ also abolished the tail current (Liu et al., *J. Pharmacol. Exp. Ther.* 287: 877–83 (1998)). These features of the delayed rectifier current (inward rectification of the time-dependent current, complete block of the tail current by E-4031, dofetilide and removal of the extracellular K$^+$) are consistent with the previous description of $I_{Kr}$ in rabbit and other species (Clay et al., (1995); and Sanguinetti et al., (1990)).

In the same cell shown in FIGS. 1A and 1B, $I_{Kr}$ current was also measured before and after E-4031 exposure. FIG. 1C demonstrates the $I_{K1}$ current elicited by a 250 ms hyperpolarization to −120 mV from a holding potential of −40 mV before and after E-4031 superfusion. Little effect was observed on the $I_{K1}$ inward current, although $I_{Kr}$ was completely blocked in the same cell. The outward holding currents that represent the amplitude of $I_{K1}$ at −40 mV before and after E-4031 superfusion were superimposable, indicating that E-4031 had no effect on the $I_{K1}$ outward current.

Figure 2:
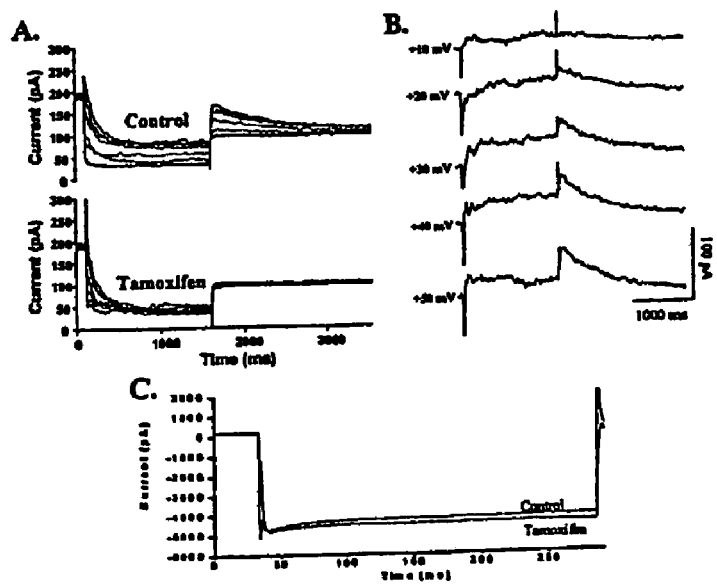
FIG. 2. Recordings of $I_{Kr}$, $I_{to}$, (A and B) and $I_{K1}$ (C) in the same cell before and after 5 minutes superfusion with 10 µmol/L tamoxifen. Panel A) $I_{Kr}$ and $I_{to}$ currents recorded before and after superfusion with tamoxifen. Tamoxifen abolished the $I_{Kr}$ tail current and also reduced the time-dependent $I_{Kr}$ current, without affecting the transient outward current ($I_{to}$); Panel B) Tamoxifen-sensitive currents obtained by digital subtraction of currents before and after tamoxifen superfusion. Note the inward rectification of the lime-dependent $I_{Kr}$ currents at very positive potentials compared with the tail currents and their similarity to the E-4031 sensitive currents; Panel C) $I_{K1}$ current recorded before and after superfusion with tamoxifen. Tamoxifen showed no block of $I_{K1}$ inward current. The outward holding currents, which represent the amplitude of $I_{K1}$ at −40 mV, were superimposed together.

Effect of Tamoxifen on $I_{Kr}$, $I_{to}$ and $I_{K1}$. The effect of tamoxifen on the three major potassium currents was tested using the same protocol as described for the experiment in FIG. 1. Shown in FIG. 2 are the $I_{Kr}$, $I_{to}$ and $I_{K1}$ currents elicited in the same cell before and after 5 minutes exposure to 10 μmol/L tamoxifen. Similar to E-4031, tamoxifen abolished the $I_{Kr}$ tail current and also reduced the time-dependent current without affecting $I_{to}$ or the holding current (FIG. 2A). The solvent for tamoxifen, ethanol, had no effect on $I_{Kr}$ at the concentration (£0.1% v/v) used to dissolve tamoxifen. FIG. 2B depicts the tamoxifen sensitive currents obtained by digital subtraction of currents in the bottom tracings from currents in the top tracings in panel A. There is a striking similarity between the tamoxifen sensitive current and the E-4031 sensitive current shown in FIG. 1B. In both FIGS. 1B and 2B, the time-dependent current demonstrated strong inward rectification at very positive potentials compared with the tail current, while $I_{to}$ was not detectable in either the tamoxifen or the E-4031 sensitive current. FIG. 2C shows the $I_{K1}$ current measured before and after 5 minutes exposure to 10 μmol/L tamoxifen in the same cell shown in FIGS. 2A and 2B. Like E-4031, tamoxifen produced no inhibition of the $I_{K1}$ inward current at −120 mV. In fact, $I_{K1}$ inward current was slightly larger after tamoxifen treatment of this cell (FIG. 2C). The outward holding currents representing the amplitude of $I_{K1}$ at −40 mV were superimposable, indicating that tamoxifen had no effect on the $I_{K1}$ outward current.

Figure 3:
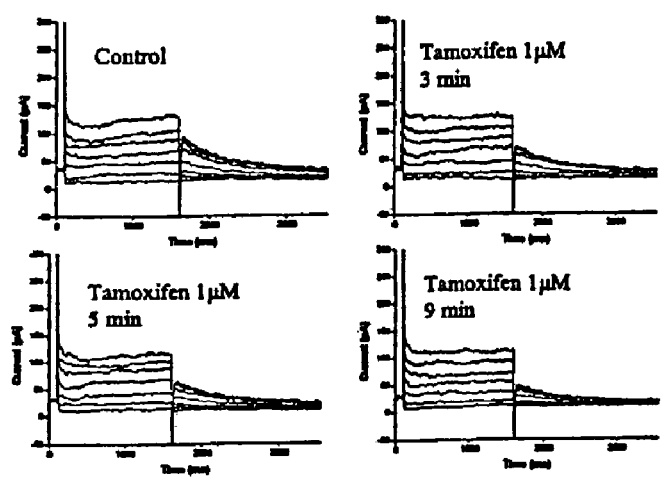
FIG. 3. Time-dependent block of $I_{Kr}$ by tamoxifen. $I_{Kr}$ currents were recorded in the same cell before drug administration, 3, 5 and 9 min. after superfusion with 1 µmol/L tamoxifen.

Time-dependent Block of $I_{Kr}$ by Tamoxifen. FIG. 3 depicts a typical experiment performed in the same cell before drug administration (control), or after 3, 5 and 9 min. superfusion with 1 μmol/L tamoxifen. As shown in FIG. 3, $I_{Kr}$ block by tamoxifen is time-dependent and has a slow onset. Further block can still be observed after superfusion for 5 minutes. In contrast, $I_{Kr}$ was readily recorded from control myocytes (no exposure to tamoxifen) for at least ten minutes without any sign of run-down. In the absence of drug, the amplitude of $I_{Kr}$ measured ten minutes after membrane rupture was 103.4±6.15% of that measured immediately after membrane rupture (n=3, p>0.05).

Figure 4:
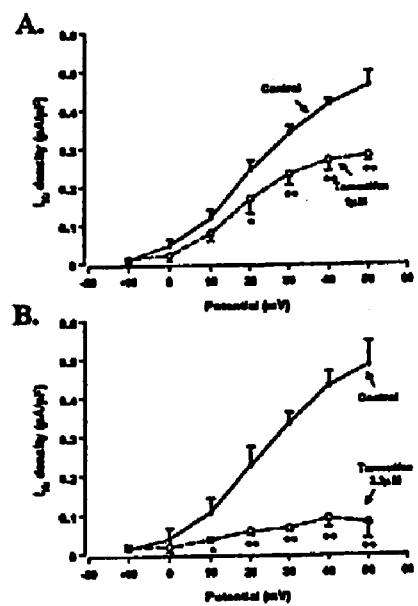
FIG. 4. Voltage- and concentration-dependent block of $I_{Kr}$ by tamoxifen. $I_{Kr}$ tail currents were measured 5–7 min. after superfusion with tamoxifen. Panel A) Effect of 1 µmol/L I-V relationship; Panel B) Effect of 3.3 µmol/L tamoxifen on I-V (current-voltage) relationship. Data are expressed as mean±SD, n=4, *p<0.05.

Effect of Tamoxifen on the I-V Relationship of $I_{Kr}$. FIGS. 4A and 4B demonstrate the effects of 1 and 3.3 μmol/L on the I-V (current-voltage) relationship of $I_{Kr}$, measured after 5–7 min. infusion of tamoxifen. Tamoxifen markedly reduced $I_{Kr}$ current amplitude in a concentration-dependent fashion. A typical voltage-dependent block of $I_{Kr}$ is shown in FIG. 4. Note the greater block at more positive potentials. At the test potential of +50 mV, tamoxifen (1 and 3.3 μmol/L) blocked $I_{Kr}$ by 39.5%±1.7% (p<0.01) and 84.8%±1.3% respectively (p<0.01). No significant block of $I_{K1}$ was observed at 3.3 μmol/L (5.5%±0.9% test potential=−120 mV, n=4, p>0.05).

Example 3

Comparison of $I_{Kr}$ Block by Tamoxifen and Quinidine

Figure 5:
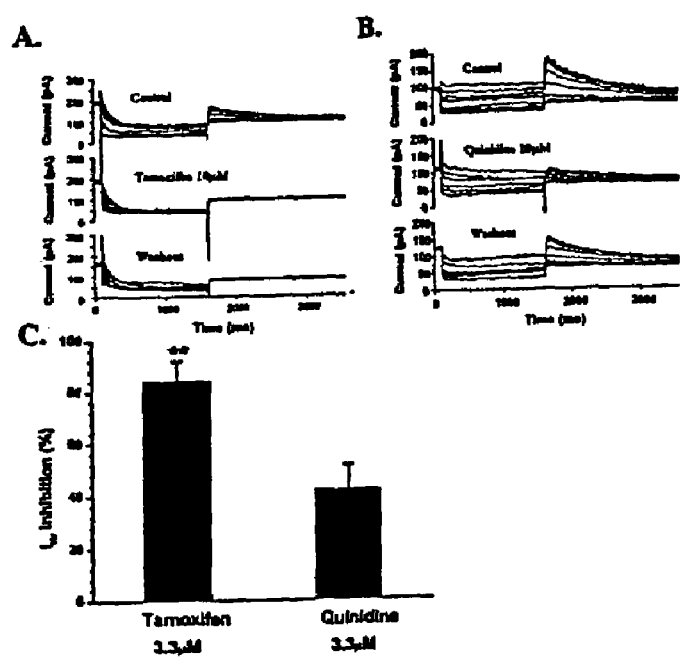
FIG. 5. Comparison of $I_{Kr}$, block by tamoxifen and quinidine. Panel A) $I_{Kr}$ currents recorded from the same cell before drug administration, 5 minutes after superfusion with 10 µmol/L tamoxifen and 5 minutes after washout. $I_{Kr}$ tail currents were abolished by tamoxifen without recovery. Panel B) $I_{Kr}$ currents recorded from another cell before drug administration. 5 minutes after superfusion with 10 µmol/L quinidine and 3 minutes after washout demonstrate that $I_{Kr}$ tail currents were reduced but not abolished by quinidine with partial recovery after 3 minutes washout. Panel C) inhibition of $I_{Kr}$ by 3.3 µmol/L tamoxifen and 3.3 µmol/L quinidine. Data are expressed as mean±SD, n=4, **p<0.01.

Quinidine is a drug that has been frequently associated with TdP (Roden et al., *Am. Heart J.* 111: 1088–93 (1986)). To compare the block of $I_{Kr}$ by tamoxifen to that produced by quinidine, we performed the protocol as discussed above, using either 10 μmol/L tamoxifen or 10 μmol/L quinidine. Tamoxifen completely blocked the $I_{Kr}$ tail current with no recovery observed after 5 min. washout, whereas the same concentration of quinidine (10 μmol/L) only partially blocked the $I_{Kr}$ tail currents, with recovery within 3 min.

washout. In other experiments, complete recovery of $I_{Kr}$ from quinidine block was usually observed after ~5 minutes washout, while no recovery from tamoxifen could be detected even after 15 minutes washout. FIG. 5C compares the percentage inhibition of $I_{Kr}$ by tamoxifen and quinidine at the same concentration of 3.3 μmol/L. These data show that, at the least potential of −50 mV, tamoxifen produced significantly greater inhibition of $I_{Kr}$ compared to quinidine (84.8%±1.3% versus 42.5%±9.1%, p<0.01). Thus, tamoxifen was a more potent and longer lasting blocker of $I_{Kr}$ than quinidine.

Figure 6:
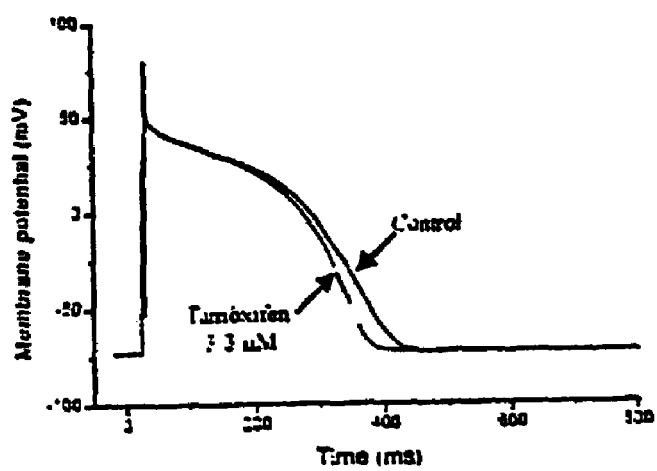
FIG. 6. Effect of tamoxifen on the action potential duration (APD). Action potentials were elicited by injecting 100 pA depolarizing currents of 2 ms, at a frequency of 0.45 HZ. Shown in the figure are two superimposed action potential tracings recorded in a single ventricular myocyte before and 4 minutes after exposure to 3.3 µmol/L tamoxifen. The two tracings are averaged tracings from 16 trials.

Effect of tamoxifen on APD and $I_{Ca}$. We next examined whether tamoxifen causes prolongation of action potential duration (APD). FIG. 6 shows action potentials recorded before and after 4 min. exposure of 3.3 μmol/L tamoxifen. Surprisingly, although tamoxifen inhibited $I_{Kr}$ by about 84.8% at this concentration, no significant prolongation of APD was observed. APD measured at 90% repolarization ($APD_{90}$) before and after about 4–5 min. superfusion of tamoxifen (3.3 μmol/L) was 341±49 ms and 332±19 ms respectively (n=16, p>0.05). Since under control conditions, no significant shortening of APD was observed in the initial 10 min. after cell membrane rupture, the absence of APD prolongation by tamoxifen was not secondary to a "run-down" phenomenon.

Figure 7:
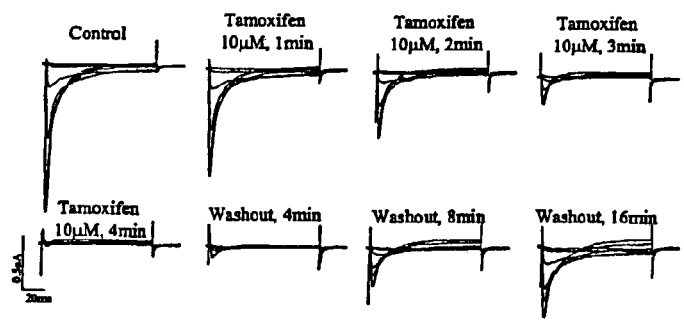
FIG. 7. Effect of tamoxifen on the L-type $I_{Ca}$. $I_{Ca}$ was recorded in the same cell before tamoxifen administration and 1, 2, 3, 4 min. after superfusion of 10 µmol/L tamoxifen and after 2, 4, 8 and 16 min. after washout. Note the marked inhibition of $I_{Ca}$ and partial recovery after washout.

This unexpected effect on APD and previous reports of $I_{Ca}$ blockade by tamoxifen (Song et al., *J. Pharmacol. Exp. Ther.* 277: 1444–53 (1996)), prompted us to study the possible effect of tamoxifen on the cardiac inward $I_{Ca}$. Consistent with earlier studies by Song et al. (1996) in vascular smooth muscle cells, we also observed a potent effect of tamoxifen in cardiac rabbit ventricular myocytes. Significant inhibition Of $I_{Ca}$ was observed at tamoxifen concentrations greater than 1 μmol/L, with almost complete inhibition observed at 10 μmol/L (FIG. 7).

Since blocking of $I_{Ca}$ will lead to a shortening of the APD, this effect may largely cancel the $I_{Kr}$ blocking effect of tamoxifen, which would otherwise lead to a prolongation of APD in single rabbit cardiomyocyte and prolongation of QT interval in whole heart. The obvious discrepancy between the obviousness in rabbit (e.g., no effect on APD) and the observations in humans (e.g., QT prolongation) may result from different relative contributions of $I_{Kr}$ or $I_{Ca}$ to the APD and/or different relative potencies of tamoxifen in blocking $I_{Kr}$ versus $I_{Ca}$ in difference species. The net effect of tamoxifen, as well as other agents, on the APD in a certain species would therefore depend on both the relative contribution of the $I_{Kr}$ versus $I_{Ca}$ to the APD and the relative potency of tamoxifen in blocking $I_{Kr}$ versus $I_{Ca}$.

Nevertheless, the major finding from these experiments (Examples 2 and 3) is that tamoxifen potently blocks the rapid component of the delayed rectifier current, $I_{Kr}$, in a voltage-, concentration- and time-dependent fashion. No significant effect of tamoxifen was observed on $I_{K1}$ or $I_{to}$ to at concentrations up to 10 μmol/L (FIG. 2). Tamoxifen blocks $I_{Kr}$ with a potency even greater than quinidine, a drug that has been shown to block $I_K$ and is associated with a high incidence of drug-induced TdP (Roden et al., (1986)). This is, to our knowledge, the first study showing that tamoxifen is a potent and relatively selective blocker.

Example 4

ECG Arrhythmia Assessment of Ibutilide

Highly accurate and reproducible measures of the QT interval in humans have been developed (Woosley et al., *Am. J. Cardiol.* 72: 36B–43B (1993); Sale et al., *Clin. Pharmacol. Ther.* 56: 295–301(1994)). ECG analysis is one method of assessing arrhythmias, such as prolonged QT intervals. Ibutilide or any other pharmaceutical agent to be studied, can be assessed using an ECG. It is preferable to administer the drug (e.g., ibutilide) intravenously. Ibutilide produces a reliable prolongation of the QT interval, and its effects dissipate rapidly. Twenty male and twenty female healthy volunteers (ages 21–40) received a single, low dose of ibutilide (0.003 mg/kg), and serial ECGs were obtained for periods before ibutilide administration (time=0), to time=4 hours (e.g., 0.5, 10, 15, 20, 30, 40, 50, 60, 90, 120, 240 and 360 minutes after administration). All ECGs were 12 lead and were recorded on a computer disc and on paper at a speed of 50 mm/sec, with the subject in a stationary, resting, supine position. ECGs were coded, randomized and blindly measured using a computer-operator interactive program, employing a validated method as previously described in ((Woosley et al., (1993); Sale et al., (1994)). Women were studied at each phase of the menstrual cycle (e.g., menses, ovulation and luteal), guided by luteinising hormone (LH) surge and confirmed with estradiol and progesterone plasma determinations. Men were studied only once. The maximum and average QT changes, after each dose of ibutilide, were compared to baseline.

Figure 8:
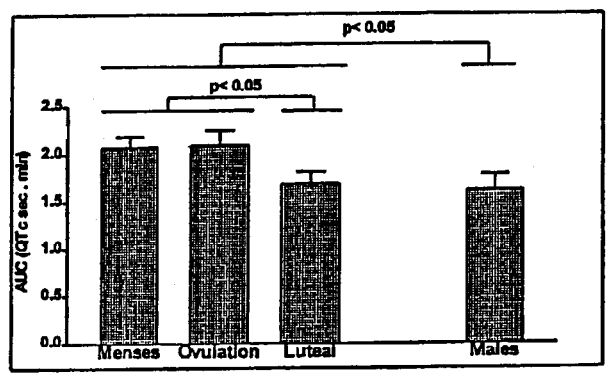
FIG. 8. Baseline QTc intervals in abdomen during the three phases of the menstrual cycle and in men. Bars indicate means and SEM, n=20 males and 20 females.
Figure 9:
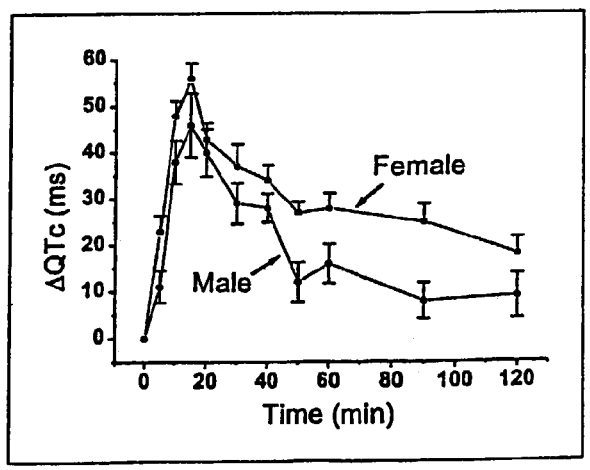
FIG. 9. Change in QTc in males and females (menstrual phase).
Figure 10:
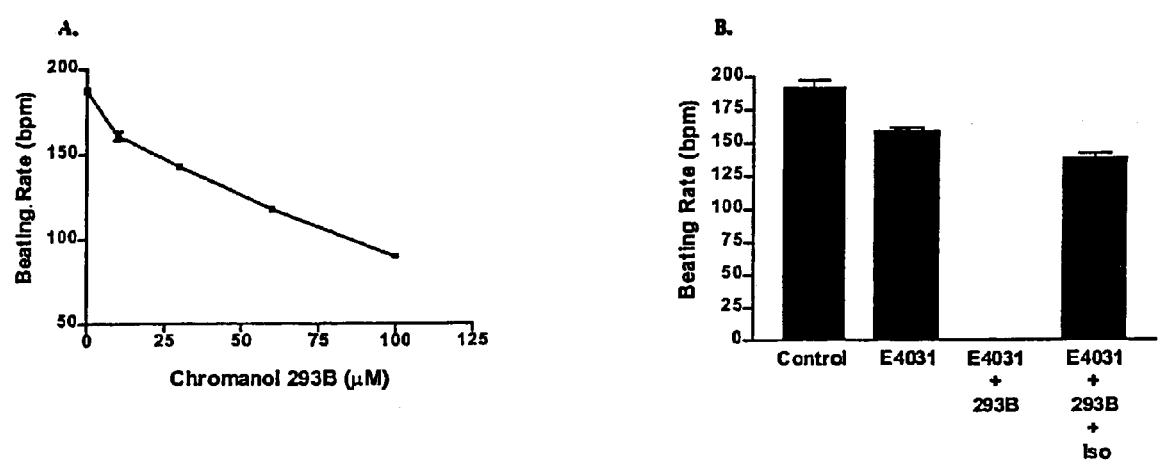
FIG. 10. Role of delayed rectifier potassium currents oil spontaneously beating cardiomyocytes. Panel A. Effect of chromanol 293B on the spontaneous beating rate in cultured neonatal rat cardiomyocytes. Panel B. Effect of E-4031 (10 μM) alone and in combination with 293 (μM) and isoproterenol (1 μM) on the spontaneous beating rate of cultured neonatal rat cardiomyocytes.

The baseline QTc of females during the menses, ovulation, and luteal phases were similar (410±15 msec, 408±15 msec, and 411±12 msec, respectfully), but, as expected, they were significantly longer than the baseline QTc in men (397±22 msec, p<0.01) (FIG. 8). To better analyze the QTc changes over time, after the ibutilide infusion, we compared the area under the curve of the change in QTc versus time over the 60 minutes after the infusion (FIG. 9); this is the period of time where both maximum therapeutic and toxic effects of the drug are expected. The mean QTc change over time was significantly smaller in men than in women (p<0.05). During the first hour, women in the luteal phase of their menstrual cycle had the least QTc prolongation secondary to ibutilide, compared to the other two phases (ANOVA p<0.05) (FIG. 9).

In the women, the maximal changes in QTc interval after the ibutilide infusion at any time interval during the menstrual, ovulation and luteal phases were 63±13, 59±17, 53±14 msec, respectively (p=ns); and in men it was 54±28 msec (p=ns). As can be seen, the QTc prolonging effect of ibutilide was prompt and was almost dissipated by the end of two hours. The mean QTc prolongation over time (AUC) after ibutilide was significantly lower for women during the luteal phase and for men compared to women during the other two phases of the menstrual cycle (p<0.05).

Example 5

Role of Delayed Rectifier Potassium Current in Spontaneously Beating Cardiomyocytes Delayed rectifier potassium channels are important components of cardiac repolarization. There are two major delayed rectifier potassium currents, $I_{Kr}$ (rapid component) and $I_{Ks}$ (slow component). Drugs that block these currents, particularly $I_{Kr}$, slow cardiac repolarization and increase the risk of developing potentially fatal cardiac arrhythmias such as Torsades de Pointes. Moreover, mutations in the genes encoding for delayed rectifier potassium channel proteins have been linked to long QT syndrome, a condition seen in patients at high risk for developing Torsades de Pointes cardiac arrhythmias and sudden death. While several specific inhibitors of $I_{Kr}$ (d-sotalol, dofetilide, E-4031) have been available for several years, studies of endogenous $I_{Ks}$ have been hampered by a lack of pharmacological tools to selectively block its activity. Recently, however, a new compound, chromanol 293B, has been reported to be a relatively selective blocker of $I_{Ks}$ (Busch et al., *Pflug. Arch.* 432: 1094–6 (1996)). In the present report, we have tested this compound using spontaneously beating cultures of neonatal rat cardiomyocytes.

In addition to the different electrophysiological properties of $I_{Kr}$ versus $I_{Ks}$ that have been described by others, these currents can be distinguished pharmacologically (Sanguinetti et al., *J. Gen. Physiol.* 96: 195–215 (1990)). For example, E-4031 (Eisai Co., Ltd., Ibaraki, Japan) has been reported to selectively block $I_{Kr}$ at concentrations up to 5–10 mM (Sanguinetti et al., (1990)), and chromanol 293B (Hoechst Marion Roussel, Frankfurt, Germany) appears to selectively block $I_{Ks}$ at concentrations up to 10–30 mM (Busch et al., (1996)). To determine if pharmacological blockade of delayed rectifier potassium currents influences the spontaneous beating rate of cultured neonatal rat cardiomyocytes, a dose-response curve was generated for chromanol 293B. As shown in FIG. 1, chromanol 293B caused a dose-dependent decrease in beating rate, but even at the highest drug concentration tested (100 mM), the reduction in beating rate was only about 50% that of control. In guinea pig ventricular myocytes, the $IC_{50}$ value for 293B inhibition of $I_{Ks}$ is approximately 2 mM, although concentrations as high as 100 mM were required to achieve complete blockade of $I_{Ks}$ in those cells (Busch et al., (1996)).

We observed a similar type of dose-response relationship with the $I_{Kr}$-blocking compound, E-4031; however, the most interesting results were observed when E-4031 and 293B were added together (Panel B). While high concentrations (5–10 mnM E-4031 and 50–100 mM 293B) of either drug alone were insufficient to completely block beating activity (maximum inhibition=50%), the combination of these two compounds totally blocked all beating activity. Remarkably, treatment with the β-adrenergic agonist, isoproterenol (0.1–1 mM), allowed for the recovery of most of the beating activity (70–80% of control values) despite the continued presence of the $I_{Kr}$ and $I_{Ks}$ inhibitors.

The simplest explanation for these results is that there may be a functional redundancy between $I_{Kr}$ and $I_{Ks}$, and complete inhibition of either current alone will cause some slowing of beating rate due to loss of repolarization capability. However, when $I_{Kr}$ and $I_{Ks}$ are both completely blocked, the cells cannot repolarize sufficiently to allow the next depolarization to occur, and hence, they stop beating. Isoproterenol appears to be able to largely overcome this inhibition, probably through its well-known stimulatory effects on calcium channels (increasing availability of $I_{Ca}$ at more positive voltages) and perhaps through direct stimulation of $I_{Ks}$ as well (Yazawa et al., *J. Physiol.* 421: 135–150 (1990); Pignier et al., *Journal of Cardiovascular Pharmacology* 31: 262–270 (1990); and Iijima et al., *J. Pharmacol. Exp. Ther.* 254: 142–146 (1990)).

All cited patents and publications referred to in this application are herein incorporated by reference in their entirety.

What is claimed is:

1. A method for determining whether a subject has a predisposition for QT interval elongation when treated with one or more pharmaceutical agents comprising the step of: (A) screening a biological sample from the subject through a nucleic acid array, wherein said nucleic acid array contains probes for a genetic mutation or polymorphism in: (1) at least one nucleic acid sequence encoding a protein mediating long QT (LQT) syndrome, and (2) at least one member selected from the group consisting of a nucleic acid sequence encoding a protein mediating multi-drug resistance (MDR) and a nucleic acid sequence encoding a cytochrome P450 enzyme.

2. The method of claim 1, wherein the nucleic acid array is a chip, a bead or a microsphere, or a microchip.

3. The method of claim 1, wherein the nucleic acid sequence encoding a protein mediating long QT (LQT) syndrome is selected from the group consisting of: LQT1, LQT2, LQT3, LQT5 and LQT6.

4. The method of claim 1, wherein the nucleic acid sequence encoding a cytochrome P450 enzyme is selected from the group consisting of: CYP1A2, CYP2C19, CYP2C9, CYP2D6, CYP2E1, CYP3A4, CYP3A5 and CYP3A7.

5. The method of claim 1, wherein the mutation or polymorphism is selected from the group consisting of: HERG (nt 1778, point mutation), KCNE1 (nt 226, point mutation), KCNQ1 (nt 217, point mutation), KCNQ1 (nt 284, point mutation), KCNQ1 (nt 475, point mutation), KCNQ1 (nt 521, point mutation), KCNQ1 (nt 629, point mutation), KCNQ1 (nt 655, point mutation), KCNQ1 (nt 659, point mutation), KCNQ1 (nt 737, point mutation), KCNQ1 (nt 746, point mutation), KCNQ1 (nt 1378, point mutation), KCNQ1 (nt 1244–1250, deletion-insertion) and SCN5A (nt 4513–4521, 9 bp deletion).

6. The method of claim 1, wherein the pharmaceutical agent is selected from the group consisting of: Amiodarone, Amitriptyline, Amoxapine, Astemizole, Azelastine, Bepridil, Chlorpromazine, Cisapride, Clarithromycin, Clemastine, Clomipramine, Desipramine, Diphenhydramine, Disopyramide, Doxepin, Erythromycin, Felbamate, Flecainide, Fluconazole, Fludrocortisone, Fluoxetine, Fluphenazine, Fluvoxamine, Foscarnet, Fosphenytoin, Halofantrine, Haloperidol, Ibutilide, Imipramine, Indapamide, Ipecac, Isradipine, Itraconazole, Ketoconazole, Levomethadyl, Maprotiline, Moexipril/HCTZ, Moricizine, Naratriptan, Nicardipine, Nortriptyline, Octreotide, Pentamidine, Perphenazine, Pimozide, Probucol, Procainamide, Prochlorperazine, Protriptyline, Quetiapine, Quinidine, Risperidone, Salmeterol, Sotalol, Sparfloxacin, Sumatriptan, Tamoxifen, Terfenadine, Thioridazine, Thiothixene, Tizanidine, Tocainide, Trifluoperazine, Trimethoprim Sulfamethoxazole, Venlafaxine and Zolmitriptan.

7. A method for determining whether a subject has a predisposition for QT interval elongation when treated with one or more pharmaceutical agents comprising the step of: (A) screening a biological sample from the subject through a DNA array, wherein said DNA array contains probes for at least two genetic mutations or polymorphisms, and wherein at least one mutation or polymorphism is located in a DNA sequence encoding a protein mediating long QT (LQT) syndrome and at least a second mutation or polymorphism is located in at least one member selected from the group consisting of a DNA sequence encoding a protein mediating multi-drug resistance (MDR) and a DNA sequence encoding a cytochrome P450 enzyme.

8. The method of claim 7, wherein the DNA sequence encoding a protein mediating long QT (LQT) syndrome is selected from the group consisting of: LQT1, LQT2, LQT3, LQT5 and LQT6.

9. The method of claim 7, wherein the DNA sequence encoding a cytochrome P450 enzyme is selected from the group consisting of: CYP1A2, CYP2C19, CYP2C9, CYP2D6, CYP2E1, CYP3A4, CYP3A5 and CYP3A7.

10. The method of claim 7, wherein the DNA array is a chip, a bead or a microsphere, or a microchip.

11. The method of claim 7, wherein the mutation or polymorphism is selected from the group consisting of: HERG (nt 1778, point mutation), KCNE1 (nt 226, point mutation), KCNQ1 (nt 217, point mutation), KCNQ1 (nt 284, point mutation), KCNQ1 (nt 475, point mutation), KCNQ1 (nt 521, point mutation), KCNQ1 (nt 629, point mutation), KCNQ1 (nt 655, point mutation), KCNQ1 (nt 659, point mutation), KCNQ1 (nt 737, point mutation), KCNQ1 (nt 746, point mutation), KCNQ1 (nt 1378, point mutation), KCNQ1 (nt 1244–1250, deletion-insertion) and SCN5A (nt 4513–4521, 9 bp deletion).

12. A nucleic acid array comprising probes for a genetic mutation or polymorphism in (1) at least one nucleic acid sequence encoding a protein mediating long QT (LQT) syndrome, and (2) at least one member selected from the group consisting of a nucleic acid sequence encoding a protein mediating multi-drug resistance (MDR) and a nucleic acid sequence encoding a cytochrome P450 enzyme.

13. The nucleic acid array of claim 12, wherein the nucleic acid sequence encoding a cytochrome P450 enzyme is selected from the group consisting of: CYP1A2, CYP2C19, CYP2C9, CYP2D6, CYP2E1, CYP3A4, CYP3A5 and CYP3A7.

14. The nucleic acid array of claim 12, wherein the nucleic acid sequence encoding a protein mediating long QT (LQT) syndrome is selected from the group consisting of LQT1, LQT2, LQT3, LQT5 and LQT6.

15. The nucleic acid array of claim 12, wherein the mutation or polymorphism is selected from the group consisting of: HERG (nt 1778, point mutation), KCNE1 (nt 226, point mutation), KCNQ1 (nt 217, point mutation), KCNQ1 (nt 284, point mutation), KCNQ1 (nt 475, point mutation), KCNQ1 (nt 521, point mutation), KCNQ1 (nt 629, point mutation), KCNQ1 (nt 655, point mutation), KCNQ1 (nt 659, point mutation), KCNQ1 (nt 737, point mutation), KCNQ1 (nt 746, point mutation), KCNQ1 (nt 1378, point mutation), KCNQ1 (nt 1244–1250, deletion-insertion) and SCN5A (nt 4513–4521, 9 bp deletion).

16. The nucleic acid array of claim 12, wherein the array is a chip, a bead or a microsphere, or a microchip.

* * * * *